US009857354B2

(12) United States Patent
Aneja et al.

(10) Patent No.: US 9,857,354 B2
(45) Date of Patent: Jan. 2, 2018

(54) COMPOSITIONS AND METHODS FOR PROGNOSIS AND TREATMENT OF NEOPLASM

(71) Applicant: NOVAZOI THERANOSTICS, INC., Plano, TX (US)

(72) Inventors: Ritu Aneja, Lilburn, GA (US); Padmashree C. G. Rida, Plano, TX (US)

(73) Assignee: NOVAZOI THERANOSTICS, INC., Plano, TX (US)

( * ) Notice: Subject to any disclaimer, the term of this patent is extended or adjusted under 35 U.S.C. 154(b) by 139 days.

(21) Appl. No.: 14/725,862

(22) Filed: May 29, 2015

(65) Prior Publication Data

US 2015/0346191 A1 Dec. 3, 2015
US 2016/0146781 A2 May 26, 2016

Related U.S. Application Data

(60) Provisional application No. 62/006,242, filed on Jun. 1, 2014.

(51) Int. Cl.
*G06F 19/00* (2011.01)
*G01N 33/50* (2006.01)
*G06F 19/10* (2011.01)
*G01N 33/574* (2006.01)

(52) U.S. Cl.
CPC ..... *G01N 33/5005* (2013.01); *G01N 33/5011* (2013.01); *G01N 33/57496* (2013.01); *G06F 19/10* (2013.01); *G06F 19/345* (2013.01); *G06F 19/3431* (2013.01); *G06F 19/3487* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

2010/0285474 A1  11/2010  Stoeber et al.

FOREIGN PATENT DOCUMENTS

WO         2012122015         9/2012

OTHER PUBLICATIONS

Bossard, Céline, et al. "Phosphohistone H3 labelling for histoprognostic grading of breast adenocarcinomas and computer-assisted determination of mitotic index." Journal of clinical pathology 59.7 (2006): 706-710.*
Jalava, P., et al. "Ki67 immunohistochemistry: a valuable marker in prognostication but with a risk of misclassification: proliferation subgroups formed based on Ki67 immunoreactivity and standardized mitotic index." Histopathology 48.6 (2006): 674-682.*
Klintman, Marie, et al. "The prognostic value of mitotic activity index (MAI), phosphohistone H3 (PPH3), cyclin B1, cyclin A, and Ki67, alone and in combinations, in node-negative premenopausal breast cancer." PLoS One 8.12 (2013): e81902.*
Perez, Edith A., et al. "Adjuvant therapy of triple negative breast cancer." Breast cancer research and treatment 120.2 (2010): 285-291.*
Skaland, Ivar, et al. "The prognostic value of the proliferation marker phosphohistone H3 (PPH3) in luminal, basal-like and triple negative phenotype invasive lymph node-negative breast cancer." Analytical Cellular Pathology 31.4 (2009): 261-271.*
Kashiwagi, Shinichiro, et al. "Advantages of adjuvant chemotherapy for patients with triple-negative breast cancer at Stage II: usefulness of prognostic markers E-cadherin and Ki67." Breast Cancer Research 13.6 (2011): R122.*
Vignon, et al., "Flow Cytometric Quantification of All Phases of the Cell Cycle and Apoptosis in a Two-Color Fluorescence Plot", PLOS One, Jul. 2013, vol. 8, Issue 7, e68425, pp. 1-8.
"Antibodies", A Laboratory Manual, (Second Edition), Edited by Edward A. Greenfield, 2014, Cold Spring Harbor Laboratory Press.
File History of U.S. Appl. No. 14/632,778, filed Feb. 26, 2015.
International Search Report issued in PCT/US2015/033293, dated Sep. 2, 2015.
Marina, et al., "Nek2 and Plk4: Prognostic Markers, Drivers of Breast Tumorigenesis and Drug Resistance", NIH Public Access, Author Manuscript, Front Biosci (Landmark Ed); Available in PMC Apr. 25, 2014, vol. 19, pp. 352-365.

* cited by examiner

*Primary Examiner* — Robert Yamasaki
(74) *Attorney, Agent, or Firm* — Ping Wang; Andrews Kurth Kenyon LLP

(57) ABSTRACT

A protocol for assessing the prognosis for a patient diagnosed with a neoplasm or suspected of having a neoplasm is provided herein. The protocol involves the steps of determining a mitotic cells to proliferating cells ratio (M:P ratio) in a neoplastic tissue sample obtained from the patient and producing a prognosis for the neoplasm based on the M:P ratio.

10 Claims, 11 Drawing Sheets

Ai

Bi

Aii

| Test | Chi-Square | DF | Pr>Chi-Square |
|---|---|---|---|
| Log-Rank | 6.053 | 1 | 0.0139 |
| Wilcoxon | 9.8891 | 1 | 0.0017 |
| -2Log(LR) | 6.1063 | 1 | 0.0135 |

Bii

| Test | Chi-Square | DF | Pr>Chi-Square |
|---|---|---|---|
| Log-Rank | 5.421 | 1 | 0.0199 |
| Wilcoxon | 4.1765 | 1 | 0.041 |
| -2Log(LR) | 6.687 | 1 | 0.0097 |

Aiii

| Stratum | 1 | 2 | Total |
|---|---|---|---|
| Threshold | Above | Below | |
| Total | 352 | 143 | 495 |
| Failed | 153 | 49 | 202 |
| Censored | 199 | 94 | 293 |
| Percent Censored | 56.53 | 65.73 | 59.19 |

Biii

| Stratum | 1 | 2 | Total |
|---|---|---|---|
| Threshold | Above | Below | |
| Total | 130 | 120 | 250 |
| Failed | 54 | 31 | 85 |
| Censored | 76 | 89 | 165 |
| Percent Censored | 58.46 | 74.17 | 66 |

KI67 + PH3 + DNA

◀ KI67 and PH3 positive cells
✷ KI67 positive cells only

FIG. 10

COMPOSITIONS AND METHODS FOR PROGNOSIS AND TREATMENT OF NEOPLASM

This application claims priority to U.S. Provisional Patent Application Ser. No. 62/006,242, filed Jun. 1, 2014. The entirety of the aforementioned application is incorporated herein by reference.

This invention was made with government support under grant number RO1 CA 169127 awarded by the National Cancer Institute (NCI) at the National Institutes of Health (NIH). The government has certain rights in the invention.

FIELD

The present invention relates to compositions and methods for predicting clinical outcomes, selecting cancer therapies, and assessing a cancer patient's response to a cancer therapy. More specifically, the methods involve compositions and methods for determining the ratio of mitotic cells to proliferating cells to aid in making these determinations.

BACKGROUND

Therapeutic planning for individualized management of breast cancer relies on patient stratification based on risk conferred by clinicopathologic factors. Prognostic and predictive markers commonly used for assessing risk associated with a breast tumor or its "aggressive potential", include expression status of cell proliferation marker Ki67, estrogen receptor (ER), progesterone receptor (PR), extent of amplification of Human Epidermal Growth Factor Receptor 2 gene, and mitotic index (MI) of the tumor.

The mitotic index (MI) is determined by counting the number of mitotic cells per 10 HPFs (high-power fields) in a section of tumor tissue and has been shown to carry a strong prognostic value. Literature reports indicate that error-prone divisions of tumor cells lead to chromosomal instability to enable generation of genetic diversity out of which superlative karyotypes can be eventually selected. Thus, the higher the mitotic frequency within the proliferative population of tumor cells, the higher the probability of aggressive clones emerging to fuel tumor progression. The mitotic score within a tumor is therefore a crucial indicator of the risk of acquiring an aggressive phenotype. However, mitosis (M-phase) is only a part of the whole proliferative cycle and is relatively infrequent, as reflected in a mean tumor doubling time of 45-325 days. Infrequent mitoses underlie the failure of drugs that specifically target the M-phase in neoplastic cells.

Another prognostic factor, the Ki67 index (KI) is defined as the percentage of Ki67-positive neoplastic cells. Ki67 protein is present during all cell cycle phases (G1, S, G2 and M) characteristic of cell proliferation. As an adjunct to tumor-grading, pathologists have long been using Ki67 immunohistochemical staining to quantify the proliferating cell population within tumors. The percentage of Ki67-positive nuclei (referred to as Ki67 Index or KI) yields crucial information about disease prognosis, predicts relative responsiveness to chemotherapy, estimates residual risk in patients on standard therapy, and serves as a dynamic biomarker for neoadjuvant treatment efficacy.

Although KI is a universally accepted prognostic marker for cell proliferation, there is tremendous ambiguity in the nomenclature of proliferation cells in diagnostic pathology. In particular, the terms "actively proliferating", "actively dividing" and "mitotically active" cells are often used synonymously. However, a cell in the "proliferation cycle" may not be actually "dividing", whereas an "actively dividing" cell is indeed "proliferating."

Among the above-described markers, MI is an integral component of the Nottingham Grading System (NGS), which is a modification of the Scarff-Bloom-Richardson breast tumor-grading system. KI measurement is not routinely mandated according to ASCO guidelines and KI has never been integrated into NGS. Extensive research has focused on evaluating KI and MI either separately or comparatively as markers of prognosis, yet surprisingly the two indices have never been studied integratively.

Tumor-grading in NGS involves microscopically evaluating three histological parameters, including tubule formation, nuclear pleomorphism, and mitotic activity/10 high-power fields (HPF), and assigning a score of 1 to 3 for each of them: tubule formation (>75%=1, 10% to 75%=2, and <10%=3), nuclear pleomorphism (none=1, moderate=2, and marked=3); and mitotic activity found in 10 HPF, based on a HPF size of 0.274 $mm^2$ (<7 mitoses=1, 7 to 14 mitoses=2, and >14 mitoses=3). Summation of the three scores thus obtained (ranging from 3 to 9) determines the placement of the tumor into one of three Nottingham Grades. A combined score of 3, 4, or 5=Nottingham Grade (NG) I; a combined score of 6 or 7=NG II; and a combined score of 8 or 9=NG III. Multivariate analyses in large cohorts of breast cancer patients have consistently demonstrated that histologic grade of a tumor is a powerful prognostic indicator of disease recurrence and patient death independent of lymph node status and tumor size.

Despite widespread use of NGS by clinicians for patient stratification, prognostic heterogeneity persists within each Nottingham Grade. One drawback of the NGS is that about 30-60% of breast tumors are categorized as Nottingham grade (NG) II (the intermediate between the lowest grade of NG I and the highest grade of NG III), a classification that is not too informative for therapeutic decision-making. Gene expression studies suggest that many of these tumors are much more similar to NG I or NG III tumors in terms of their expression profiles, implying that many NG II patients may be either overtreated or undertreated. Also, the recommendation of cytotoxic chemotherapy for all invasive lesions is far from ideal when one considers that node-negative tumors smaller than 10 mm have survival rates of >90% without chemotherapy. Hence there is a need to refine the NGS and enhance its prognostic accuracy by identifying quantifiable biomarkers for breast tumors that (i) can discriminate more sharply the risk posed by breast tumors, (ii) can be accurately and reliably determined via a clinically-facile method, (iii) are robust and applicable in some, if not all, of the subtypes of breast carcinomas, and (iv) yield more accurate patient stratification.

The accuracy of NGS cannot be improved unless the precision in determining its constituent parameters is enhanced. One source of error pertains to mis-estimation of mitotic cells due to visual recognition from hematoxylin-eosin (H&E)-stained slides (an inherently error-prone process) and subjectivity (both intra- and inter-observer) arising from different choices of regions to be assessed.

A second source of error pertains to current diagnostic practices that take MI and KI into consideration as independent entities, while in reality, mitosis is a cell-cycle phase snugly nested within the proliferative cycle. In the absence of a unified view of mitosis and proliferation, the kinetic information on how fast the proliferative tumor cell population is actually cycling is lost. There is a need to improve the accuracy of tumor grading and more optimal selection of therapies.

SUMMARY

In one aspect, method of assessing the prognosis for a patient diagnosed with a neoplasm or suspected of having a neoplasm includes the steps of: (a) exposing at least a portion of a neoplastic tissue sample from the patient to two binding agents under conditions sufficient to allow binding to pre-selected markers within the sample portion, where a first binding agent specifically targets mitotic cells in the sample portion and a second agent specifically targets proliferating cells in the sample portion; (b) exposing the sample portion in step (a) to detection reagents suitable for visualizing and discriminating between proliferating cells that are mitotic and proliferating cells that are non-mitotic; (c) determining the ratio of mitotic cells to proliferating cells (M:P ratio) within the sample portion; and (d) providing a prognosis based on the M:P ratio and the type of neoplasm.

In certain embodiments, this method can aid in determining whether a patient will benefit from an anti-mitotic or anti-microtubule therapy or chemotherapy. In other embodiments, this method can aid in determining the extent of intratumoral heterogeneity.

In some embodiments, the method further includes the step of determining the histological grade of the cancer, based on a conventional grading system, and further adjusting the histological grade of the cancer based on the M:P ratio.

The patient may be suspected of having a neoplasm or may have already been diagnosed with a neoplasm. In some embodiments, the patient has been diagnosed with malignant neoplasm, such as cancer. In one embodiment, the patient has a carcinoma. In certain preferred embodiments, the patient has been diagnosed with abreast neoplasm or breast cancer.

In one embodiment, an M:P ratio above a predetermined threshold level differentiates patients having a Luminal A subtype of breast cancer from patients having a Luminal B subtype of breast cancer.

In some embodiments, an M:P ratio above a predetermined threshold indicates a worse prognosis for a patient with Luminal B subtype breast cancer or triple negative breast cancer (TNBC). In general, among Nottingham Grade-matched tumors of luminal B or TNBC subtypes, the higher the M:P ratio or the equivalent thereto, the greater the intratumoral heterogeneity and the poorer the patient's prognosis.

In another embodiment, the patient has been diagnosed with a prostate neoplasm or prostate cancer.

In some embodiments, the determination step includes flow cytometry to determine the percentages of mitotic cells and proliferating cells. In one embodiment, additional markers are labeled to ensure that only tumor/neoplastic cells are analyzed. In other embodiments, the determination step employs an image analysis step employing a computer readable medium, wherein a nuclear segmentation step aids in the identification of cells that are mitotic or proliferative and the computer readable medium determines the percentages of mitotic cells and proliferating cells. Alternatively, serial sections are stained with hematoxylin-eosin (H&E) and/or stained for a neoplastic markers and/or markers specific for non-neoplastic cells, whereby multi-stained images of mitotic neoplastic cells, proliferative neoplastic cells and non-neoplastic cells are overlaid over one another to identify cancer cells and tumor regions unequivocally. This "virtual multiple staining" strategy ensures that stromal cells, immune cells and other non-tumor cells are not quantitated in the analysis. In another embodiment, in addition to staining mitotic and proliferative cells, multiplexed immunohistochemistry (IHC) may be used to stain for tumor-specific antigens or non-tumor antigens in the same sample sections to distinguish tumor cells from non-tumor cells surrounding or infiltrating the tissue.

In some embodiments, the first binding agent and the second binding agent is an antibody or a biologically active fragment thereof. In certain preferred embodiments, the first binding agent targets a phosphorylated form of histone H3 and the second binding agent targets Ki-67. The sample may be exposed to the first and second binding agents separately or simultaneously. In some embodiments, the method may further include the step of exposing the sample to a DNA binding agent.

The sample may be collected from a variety of different tissues. In some embodiments, the sample is a histological tissue section. In other embodiments, the sample includes whole blood, leukocytes or a cell suspension prepared from a tissue sample.

In some embodiments, the patient is treated with at least one antineoplastic agent based on the results from the M:P ratio determination. In certain embodiments, the antineoplastic agent is an anti-mitotic agent, an anti-interphase agent, an anti-microtubule agent, an anthracycline-based agents or an aromatase inhibitor agent. In other embodiments, the antineoplastic agent is a centrosome declustering agent.

In another aspect, a method of identifying a potential chemotherapeutic agent for cancer includes the steps of: (a) exposing a first group of the neoplastic cells to two binding agents under conditions sufficient to allow the binding agents to bind pre-selected markers within the first group of neoplastic cells, wherein a first binding agent specifically targets mitotic cells in the first group of neoplastic cells and a second agent specifically targets proliferating cells in the first group of neoplastic cells; (b) exposing the first portion of neoplastic cells to detection reagents suitable for visualizing and discriminating between proliferating cells that are mitotic and proliferating cells that are non-mitotic; (c) determining a first ratio of percent mitotic cells to percent proliferating cells within the first group of neoplastic cells; (d) treating a second group of the neoplastic cells with a candidate chemotherapeutic agent; (e) exposing the treated cells in step (d) to the two binding agents in step (a) under conditions sufficient to allow the binding agents to bind pre-selected markers within the treated neoplastic cells; (f) exposing the treated neoplastic cells in step (e) to the detection reagents in step (b); (g) determining a second ratio of percent mitotic cells to percent proliferating cells within the treated neoplastic cells; and (h) determining whether the second ratio is reduced in comparison to the first ratio, wherein a candidate chemotherapeutic agent that reduces the first ratio is a potential chemotherapeutic agent.

In some embodiments, the first group and the second group of neoplastic cells are cultured neoplastic cells. In other embodiments, the first group and the second group of neoplastic cells are cells located in vivo, such as cells in an in vivo tumor model. For example, a plurality of neoplastic cells can be injected into mice to form tumors in vivo, whereby the mice can be subjected to various treatment modalities and regimens comprising one or more candidate therapeutic drugs to determine the responsiveness of the mice to these drugs.

In other embodiments, a method of identifying a chemotherapeutic agent for neoplastic tissues includes the steps of: (a) exposing at least a portion of a neoplastic tissue sample to two binding agents for a time and under conditions sufficient to allow the agents to bind pre-selected markers within the sample portion, wherein a first binding agent specifically targets mitotic cells in the sample portion and a second binding agent specifically targets proliferating cells in the sample portion; (b) exposing the sample portion in step (a) to detection reagents suitable for visualizing and discriminating between proliferating cells that are mitotic and proliferating cells that are non-mitotic; (c) determining a first ratio of percent mitotic cells to percent proliferating cells within the sample portion; (d) treating the patient with a candidate chemotherapeutic agent; (e) providing a tissue sample from the treated patient, wherein the tissue sample is suspected of including neoplastic cells; (f) exposing at least a portion of the sample in step (e) to the two binding agents in step (a); (g) exposing the sample portion in step (f) to the detection reagents in step (b); (h) determining a second ratio of percent mitotic cells to percent proliferating cells within the sample portion from the treated patient; and (i) determining whether the second ratio is reduced in comparison to the first ratio, wherein a candidate chemotherapeutic agent that reduces the first ratio is a potential neoadjuvant chemotherapeutic agent.

In another aspect, a method of improving a grading system for neoplastic tissue is provided where the revised grading system comprises generating a new score (Ki67-Adjusted Mitotic Score, or KAMS) derived by using MI and KI scores determined by conventional methods (e.g., in different fields of view from different slides) and then using these numbers to approximate the quotient of percent mitotic cells divided by percent Ki67-positive cells as further described below.

In another aspect, a method of improving a grading system for neoplastic tissue is provided where the revised grading system includes analysis of cellular mitosis, and cellular proliferation in which the method substitutes for conventional analyses of cellular mitosis and/or cellular proliferation in the grading system, whereby an analysis of the M:P ratio is determined based on the percent mitotic cells to percent proliferating cells in a common tissue sample.

In another aspect, a composition includes a cocktail of two cell cycle specific binding agents, including or consisting of a first binding agent specifically targeting mitotic cells in a sample, and a second binding agent specifically targeting proliferating cells in the sample. In certain preferred embodiments, the first binding agent binds to a phosphorylated form of histone 113 and the second binding agent binds Ki-67. In another embodiment, the cocktail further includes a third binding agent that binds DNA.

In another aspect, a kit for assessing the prognosis for a patient who has been diagnosed with a neoplasm includes a first binding agent specifically targeting mitotic cells in a sample; a second binding agent specifically targeting proliferating cells in a sample; one or more detection reagents for visualizing bound complexes indicative of mitotic and proliferative cells; and instructions for use. In certain embodiments, the first and second binding agents are combined in the same container.

BRIEF DESCRIPTION OF THE DRAWINGS

FIG. 10 depicts the extraction and integration of KI and MI to derive M:P ratio from the same microscopic field using dual antibody immunohistochemistry.

DETAILED DESCRIPTION

Figure 1:
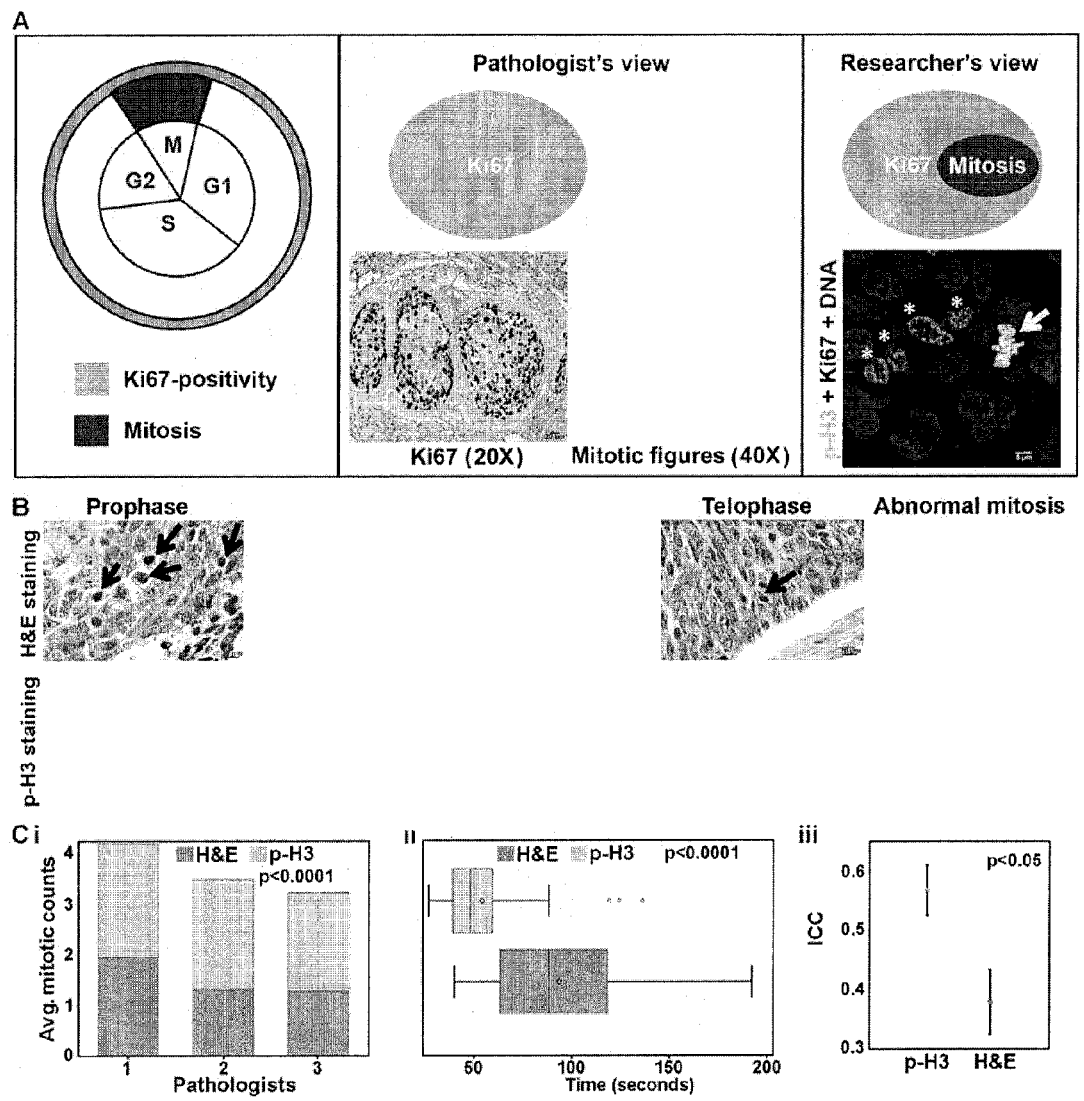
FIG. 1, Panel A schematically depicts the divergent perspectives of a pathologist and a researcher regarding an actively dividing cell. Whereas a pathologist views Ki67-positivity and mitosis as two mutually-exclusive events in cell-cycle, a researcher views mitosis as a subset of the full cycle of a proliferating or Ki67-positive cell. Panel B shows micrographs depicting various stages of mitosis in an H&E-stained paraffin-embedded breast tumor tissue section. Scale bar is 20 µm. Panel C compares mitotic count determinations from H&E-stained and p-H3-stained slides. Panel Ci depicts bar-graphs representing average mitotic counts determined by counting mitotic figures from H&E-stained or p-H3-stained slides, by each of the three pathologists. Panel Cii depicts box and whisker plots representing the average time taken by the three pathologists to score H&E-stained or p-H3-stained slides. Panel Ciii depicts a mean and standard deviation plot showing the difference in the ICC of p-H3-based versus H&E-based counting, with the confidence intervals. (t-test $p<0.05$).

A protocol for assessing the prognosis for a patient diagnosed with a neoplasm or suspected of having a neoplasm (such as cancer or benign tumor) and in treating cancer patients is provided herein. Any patient (e.g., a human of any age, gender, or ethnicity) diagnosed with a neoplasm or suspected of having a neoplasm may be selected as a subject for the present methods. The accompanying descriptions serve to illustrate, but do not limit, the invention.

Definitions

As used herein, the term "neoplastic tissue," "neoplastic cells," or "neoplasms" refers to an abnormal mass of tissue or a proliferation of cells. The growth of neoplastic cells exceeds that of normal tissue around it and it is not coordinated with that of the normal tissue around it. Neoplasms may be benign (e.g., benign tumor and atypical hyperplasia), pre-malignant (e.g., carcinoma in situ and pre-cancer) or malignant (e.g., cancer). The term "cancer" refers to any of the various malignant neoplasms characterized by the proliferation of cells that have the capability to invade surrounding tissue and/or metastasize to new colonization sites, including but not limited to leukemias, lymphomas, carcinomas, melanomas, sarcomas, germ cell tumors and blastomas. Exemplary cancers include cancers of the brain, bladder, breast, cervix, colon, head and neck, kidney, lung, non-small cell lung, mesothelioma, ovary, prostate, stomach and uterus, leukemia and medulloblastoma.

Neoplastic tissues can originate from any cell type or tissue found in a mammal, including, but not limited to hepatic, skin, breast, prostate, neural, optic, intestinal, cardiac, vasculature, lymph, spleen, renal, bladder, lung, muscle, connective, tissue, pancreatic, pituitary, endocrine, reproductive organs, bone, and blood. The neoplastic tissue for analysis may include any type of solid tumor or hematological cancer. In some embodiments, the neoplastic tissue is a breast cancer tissue. In other embodiments, the neoplastic tissue is a breast tissue with atypical hyperplasia.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which arises from transformed cells of mesenchymal origin. Sarcomas are malignant tumors of the connective tissue and are generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Methods for Prognosis of Patients Diagnosed with a Neoplastic Condition

Independent determinations of KI and MI to date, coupled with their disjointed consideration in decision-making (which disregards the fact that mitosis is an integral part of the proliferative cell-cycle), fail to harness their full prognostic potential. Notwithstanding differences of opinion concerning the relative merits of KI and MI, it is indisputable that faster tumor growth is a sign of more aggressive disease. Faster tumor growth can result from two possible scenarios: (i) KI increases and MI increases proportionally with KI, or (ii) both KI and MI increase but MI does not increase proportionally to the increase in KI. Moreover, recent studies have clearly divulged that majority of cells within proliferative cell population in a tumor, are not actually dividing (i.e., are not in M-phase of cell-cycle) but are instead, populating interphase. The more speedily cells transit through the cell-cycle, the higher will be the proportion of mitotic cells observed in the proliferating population.

The present application utilizes a novel metric that rationally integrates KI and MI into a ratio for prognosis and treatment of neoplastic conditions. This new metric, the M-to-P ratio (or M:P ratio), reveals the cycling kinetics of the proliferative cells in a tumor. These kinetics change as the agenda of a tumor evolves. By capturing this "kinetics" element, the M-to-P ratio directly measures the proportion of proliferative cells that pose an immediate threat of engendering highly aggressive progeny cells due to erroneous mitoses that could drive chromosomal instability and intratumoral heterogeneity. The M-to-P ratio of a sample thus illuminates a fundamental aspect of that tumor's biology and its quantitation measures the risk of a tumor being or rapidly become metastatic. This metric also enables deeper risk-segmentation of patients (based on their cell cycling kinetics of their neoplastic tissues) into prognostically meaningful subgroups to improve selection of a more appropriate treatment regimen for patients.

The inventors of the present application have discovered that independent determinations of the Ki67 index (KI) and the mitosis index (MI) in different fields of view from different slides fail to harness their full prognostic potential. Further, it was discovered that the previous prognostic accuracy of MI was compromised by subjectivity and errors in visual determination. To establish this, the inventors first brought KI and MI on the same measurement scale. Specifically, the inventors obtained the clinicopathologic data for a large cohort of breast carcinoma cases from three different hospitals (Nottingham University Hospital, UK; Emory University Hospital, Atlanta, US; and Northside Hospital, Atlanta, US).

In all three hospitals, only mitotic score information was available for all patients. Therefore, the inventors first converted MI (categorical-variable) into a mitotic cell percentage. Briefly, 10 HPFs were evaluated in at least 5 patient samples and on average had ~500 cells. Average mitotic cell counts were determined for each mitotic score category by counting the number of mitotic cells in 10 HPFs for a total of 267 cases (140 cases from Emory University Hospital and 127 cases from Northside Hospital) spanning all three Nottingham grades. It was then determined that the average mitotic counts for Mitotic Scores 1, 2, and 3 are 2.94, 11.12 and 32.62, respectively. These mitotic cell counts provided an estimate of number of mitotic cells per 500 cells (10 HPFs), thus providing the mitotic cell percentage.

A Ki67-Adjusted mitotic score (KAMS) for each patient was calculated simply as quotient of percent mitotic cells divided by percent Ki67-positive cells. A KAMS determination utilizes the KI and MI information of a given sample as these indices are currently derived, namely, from different slides (and therefore different microscopic fields of view), and from totally different scales of measurement (MI is determined as total mitotic cells in 10 HPFs while KI is the percentage of nuclei that stain positive for Ki67). Based on the concept that the more speedily cells transit through the cell-cycle, the higher will be the proportion of mitotic cells observed in the proliferating population, the inventors reasoned that the ratio of the number of mitotic cells in a field of view to the number of proliferating cells in the same microscopic field of view (or the mitosis-to-proliferation ratio; or M:P ratio) would provide the most direct and accurate measurement of cell cycling kinetics within a sample.

KAMS analysis of the Nottingham University dataset revealed that NG II and NG III can be further segmented into "high cycling kinetics" and "low cycling kinetics" subclasses with prognosis (as assessed by the patients' clinical outcomes such as breast cancer-specific survival, progression-free survival, metastasis-free survival and overall survival) that were statistically different from each other. These results show that KAMS can uncover a new layer of information about the cell cycle kinetics in tumor samples; this information was previously overlooked in the Nottingham Breast Tumor Grading System which does not integrate the information provided by MI and KI.

Figure 2:
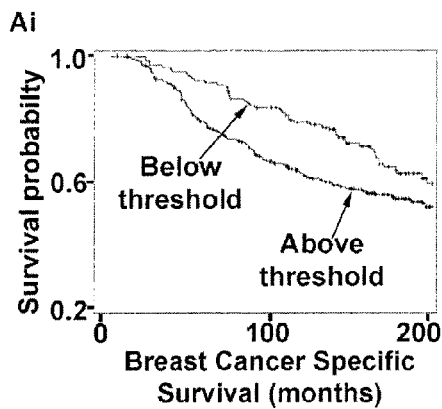
FIG. 2 depicts Kaplan-Meier survival plots (Breast cancer-specific survival) showing stratification of Lum B and TNBC patients (n=495) from the Nottingham University dataset.
Figure 2:
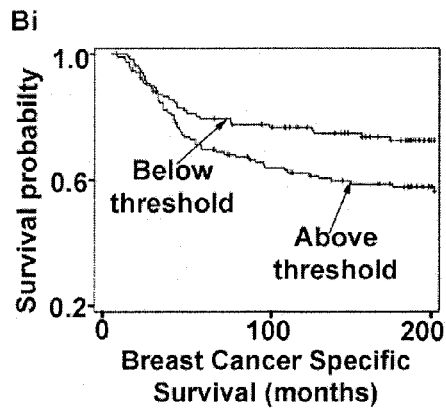
Figure 3:
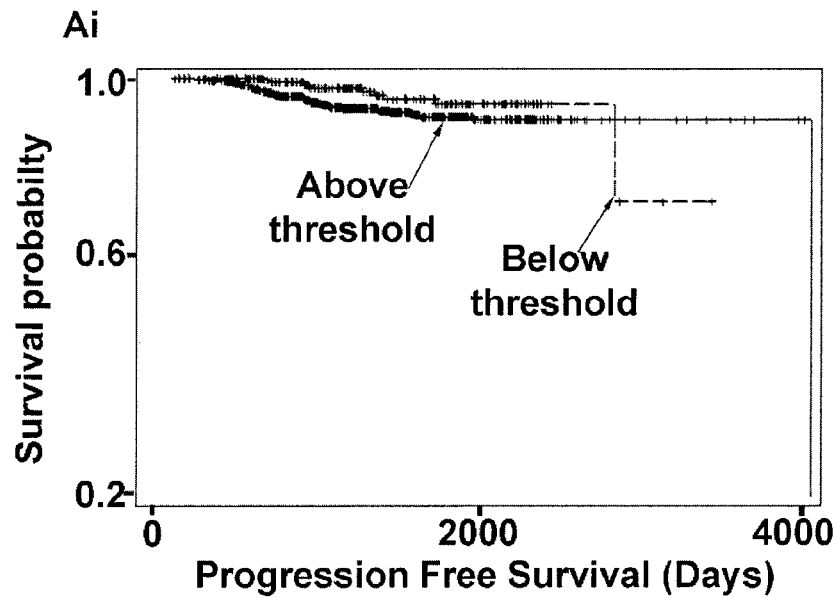
FIG. 3 depicts Kaplan-Meier survival plots (Progression-free survival) showing stratification of a combined set of Lum B and TNBC patients (n=1070) from the Emory University dataset.
Figure 4:
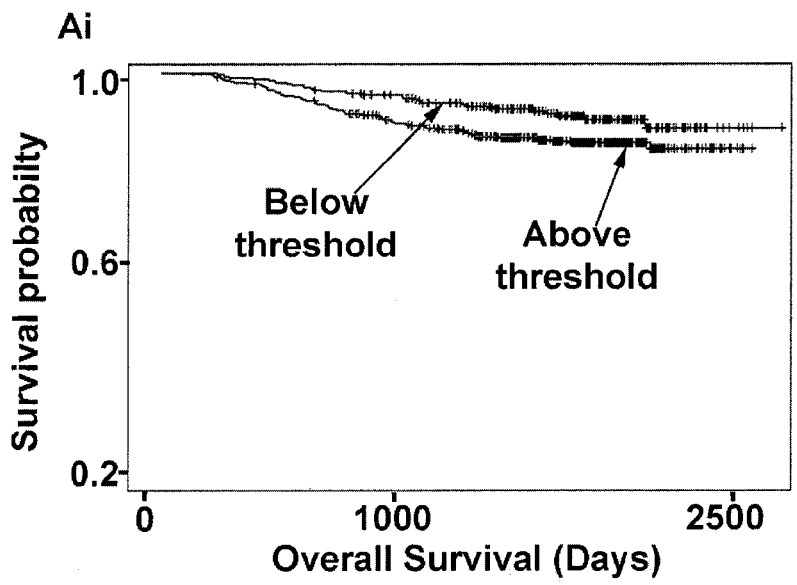
FIG. 4 depicts Kaplan-Meier survival plots (Overall survival) showing stratification of a combined set of Lum B and TNBC patients (n=880) from the Northside Hospital dataset.

As shown below, KAMS has the ability to stratify a combined cohort comprising Luminal B (defined as samples that are ER+ and/or PR+, Her2+ and ER+ and/or PR+, Her2− with KI of 15% or above) and triple-negative breast cancers (TNBCs) drawn from all three Nottingham Grades into two subclasses with different cell cycling kinetics, in all three datasets assessed by the inventors (FIGS. 2-4). The low KAMS (low cycling kinetics, lower-risk) subclass had better outcomes that were very similar to that of NG II patients; the high KAMS (high cycling kinetics, high-risk) subclass had poorer outcomes that were very close to that of NG III patients. These data show that KAMS and cell cycling kinetics have prognostic value in Luminal B and TNBC patients. In particular, these data also show that a KAMS determination in Luminal B and TNBC patients can aid in discerning subgroups of patients that possess greater ITH and bear a higher risk of metastasis and therapy resistance than others.

Figure 6:
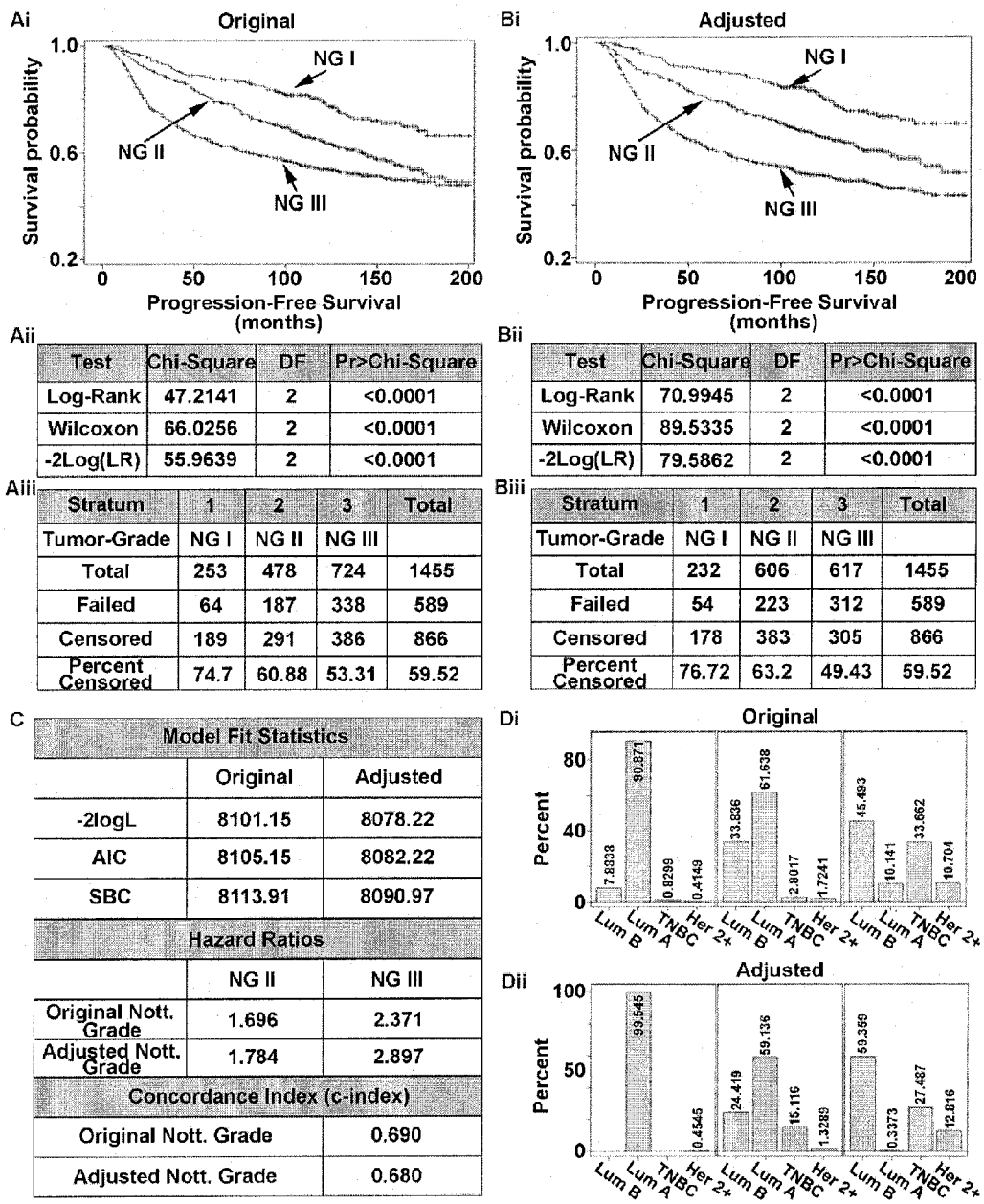
FIG. 6 shows the histological grades of 1455 patients from the Nottingham University dataset (for whom progression-free survival data was available) and grades adjusted according to the grade adjustment model depicted in FIG. 5.
Figure 7:
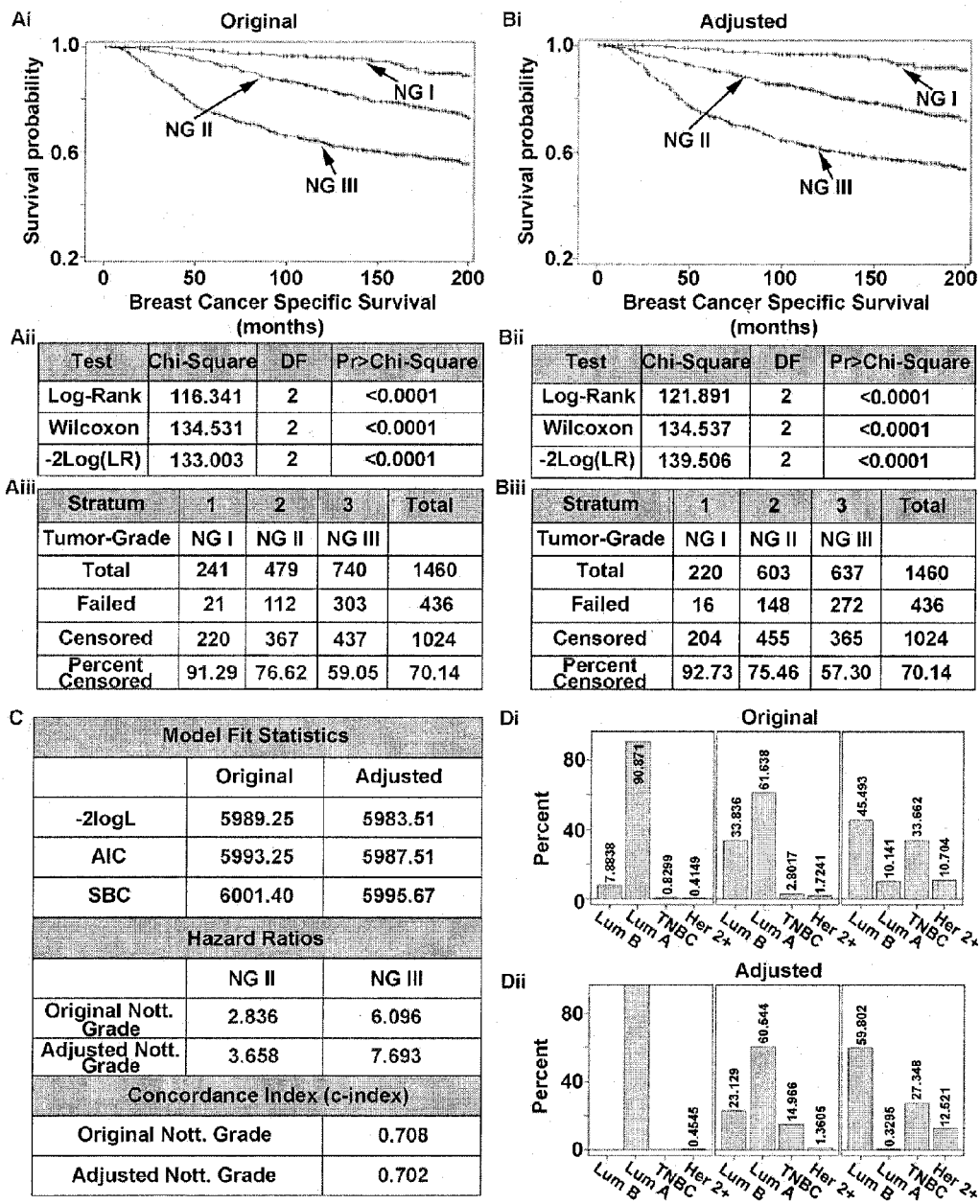
FIG. 7 shows the histological grades of 1460 patients from the Nottingham University dataset (for whom breast cancer-specific survival data was available) and grades adjusted according to the grade adjustment model depicted in FIG. 5.

The inventors then evaluated the effectiveness of using KAMS as a classifier for improving patient risk-stratification in the Nottingham University dataset. The threshold KAMS value that best stratifies Luminal B and TNBC patients into a high cycling kinetics (higher-risk) and low cycling kinetics (lower-risk) subclasses with significantly different survival probabilities ($p<0.05$) was determined (FIG. 5) and log-rank tests were performed for breast cancer specific survival (BCSS) and progression-free survival (PFS) (FIGS. 6 and 7).

Low cycling kinetics Luminal B and TNBC patients were found to have outcomes that closely match those of patients originally in NGII; this subclass of Luminal B and TNBC patients were therefore moved into the "Adjusted NG II" category. Similarly, high cycling kinetics Luminal B and TNBC patients were found to have outcomes that closely match those of patients originally in NG III; the high cycling kinetics subclass of Luminal B and TNBC patients were therefore moved into the "Adjusted NG III" category. Following this grade adjustment and re-stratification of patients in the Nottingham University dataset, the inventors' grade adjustment model was found to have much better model fit statistics and hazard ratios (FIGS. 6 and 7) than the original Nottingham Grading System indicating the strong risk-predictive value of KAMS above and beyond that provided by NG variables.

Figure 8:
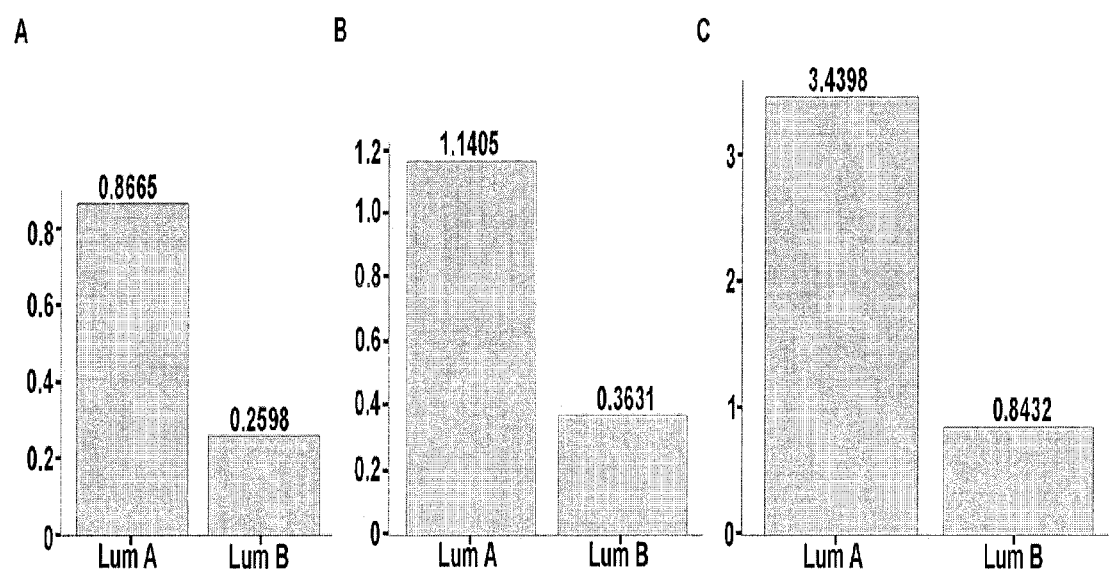
FIG. 8 depicts the mean KAMS values of Lum A and Lum B patients in NG I, NG II and NG III, respectively, in a combined dataset comprising patients from Northside Hospital, Atlanta, Emory University Hospital, Atlanta and Nottingham University Hospital, UK.

Further, as shown below, KAMS can be used to distinguish Luminal A and Luminal B subtypes in the clinic since they have very significantly different and characteristic cell cycling kinetics (FIG. 8).

Immunofluorescence-based (FIG. 9) and immunohistochemistry-based (FIG. 10) methods may be used to determine the M:P ratio in clinical samples. Accordingly, the M:P ratio metric can provide a measure of mitotic propensity of a proliferative population and a measure of the risk posed by the proliferative population due to erroneous mitoses that could drive chromosomal instability and intratumoral heterogeneity. The present methods reduce inter-observer variability, enhance the reproducibility and accuracy of MI determinations, and may be used to risk stratify NG and KI-based groups, which has profound clinical implications as further elaborated below.

In one aspect, a method of assessing the prognosis for a patient who has been diagnosed with a neoplastic condition, includes the step of providing a tissue sample suspected of containing neoplastic cells from the patient and exposing at least a portion of the sample to at least two binding agents under conditions sufficient for binding the binding agents to the neoplastic cells. Whereas the first binding agent specifically targets all mitotic cells in the sample portion, the second binding agent specifically targets all proliferating cells in the sample portion. Upon binding of the binding agents to the cells, the sample is further exposed to detection reagents suitable for visualizing proliferating cells and discriminating between proliferating cells that are mitotic and proliferating cells that are non-mitotic. Following this step, the M:P ratio within a common portion of the sample is determined.

A serial section of the sample that has been stained with hematoxylin-eosin, or stained with a cancer-specific marker, or a marker that labels only non-cancer cells, is then processed for either immunohistochemical visualization, immunofluorescence visualization, or visualization using quantum dots to ensure that the region of the sample being profiled for M:P ratio comprises tumor cells only. The determination of M:P ratio in a clinical tissue sample could be combined with methods that allow the visualization of apoptotic cells (marked by a marker for apoptosis) that would allow quantification of net tumor growth kinetics (arising from the addition of new cells via mitoses in the proliferative population within a tumor, minus the loss of cells due to apoptosis).

In certain embodiments, determination of M:P scores in tissue samples or tissue sections may include staining and imaging of a tissue sample (e.g., whole-slide imaging or imaging of specific regions of interest), whereby the image analysis is carried out to determine mitotic and proliferative cells. From these images, an M:P ratio can be quantitated in areas deemed as Ki67 "hot-spots" exclusively, or from both "Ki67 Hotspots" and "Ki67 non-hotspot regions" after giving appropriate weights to these types of regions. In addition, M:P ratios may be derived from "Mitotic hotspots" and regions that are not "mitotic hotspots" after giving these types of regions appropriate weights.

An M:P ratio may be derived from any region of interest or from multiple regions after giving them appropriate weights (e.g., M:P ratios in regions that show high expression of certain biomarkers or high CAS (see below) may have special prognostic significance). In each case, an optimal scoring method may be determined via retrospective studies of samples with known clinical outcomes, whereby the weighted model providing the best concordance with clinical outcomes would be selected as the M:P ratio scoring method. Preferably, these image analysis steps are computer-aided with the use of appropriate software.

In contrast to determining the mitotic index (MI) and nuclear Ki67 positivity as two independent variables, the present method determines the proportion of mitotic cells within all of the proliferating cell pool in a common field. Mitotic cell positivity may be scored as the total number of cells expressing an M-phase specific marker that can be labeled with a suitable M-phase specific binding agent (e.g., "first binding agent"). Proliferative cell positivity may be scored as the total number of cells selectively expressing a marker during all proliferative phases of the cell cycle (i.e., G1, S, G2 and M). Nuclear Ki67 antigen is an exemplary proliferative cell marker that can be tracked using a suitable "second binding agent," such as an anti-Ki67 antibody. Within the population of proliferating cells in a portion of the tissue sample, a subpopulation of mitotic (M phase) cells exists, where the proportion of mitotic cells to proliferating cells defines the M:P ratio.

The tissue sample can be manipulated by, for example, sectioning or dissociation, and exposed to the first and second binding agents, either sequentially or simultaneously, for a time and under conditions sufficient to allow the agents to detectably label cells within the sample.

M:P ratios reveal the dynamic agenda of an evolving tumor and provides highly actionable information that can aid risk stratification of unselected cohorts of operable early-stage breast cancer patients, especially those with Luminal B and TNBC subtypes. Incorporation of a M:P ratio thus maximizes the use of available biomarker information to facilitate personalized medicine for breast cancer management.

In certain embodiments, a portion of the patient's tissue may be further analyzed to quantitate the numeric degree and structural degree of centrosomal amplification. Centrosome amplification is a key driver of chromosomal instability that underlies the generation of karyotypic diversity and the evolution of more aggressive and malevolent phenotypes such as metastases and therapeutic resistance. Quantitation of centrosome amplification can include the steps of: (a) processing a sample of tumor tissue or neoplastic cells from the patient in a form suitable for visualization and demarcation of cell nuclei, individually distinguishable centrosomes (iCTRs) and megacentrosomes (mCTRs) in a region of interest (ROI) defined by a plurality of cell nuclei; (b) determining the numbers of iCTRs and mCTRs associated with each cell nucleus in the ROI; (c) determining the volume of each mCTR in the ROI; and (d) calculating one or more centrosome amplification scores (CASs) values for the sample based on steps (b) and (c), wherein the one or more CASs indicate the severity of centrosome amplification, the frequency of centrosome amplification, or both, and wherein the one or more scores provide a measure of a level of risk and/or a prognosis associated with the neoplastic tissue.

Intratumoral heterogeneity (ITH) in cancers is crucial for orchestrating the growth, survival, invasion and spread of cancer cells in a patient's body. The generation of ITH and metastatic clones relies on frequent passage of cancer cells through error-prone mitoses.

Information from M:P scores and CAS scores can provide an important measure of the rate at which intratumoral heterogeneity is being generated, thereby providing a better prediction of metastatic risk and therapy resistance. The higher the M:P ratio and CAS scores, the greater the intratumoral heterogeneity and the poorer the patient's prognosis. Further integrating CAS scores into this analysis can further improve the assessment of intratumoral heterogeneity to more accurately predict a patient's prognosis, including metastatic risk, and provide a more rational, efficacious basis for treatment.

For example, in some embodiments images of tissue samples that have been stained for mitotic and proliferative cells may be overlaid with images of serial sections stained for a variety of biomarkers, including amplified centrosomes. This can provide new cumulative measures of risk that combine M:P ratio with different biomarkers so as to provide more appropriate weightage to the M:P ratio. Thus, these other biomarkers can be employed for more accurate risk prognostication and selection of more optimal therapies.

The M:P ratios or the cumulative measures of risk described above could also be used in conjunction with clinicopathological variables routinely determined in the clinic, including the results of other risk-predictive tests (such as Oncotype Dx) or gene-expression information to yield new risk models for improved patient stratification and personalization of cancer treatment.

Compositions and Kits

In another aspect, the present application provides compositions and kits for the prognosis methods described herein. In one embodiment, the composition includes a cocktail of two cell cycle specific binding agents. The first binding agent specifically targets all mitotic cells in a sample. The second binding agent specifically targets all proliferating cells in the sample. In another embodiment, the cocktail consists of the first binding agent specifically targeting all mitotic cells in a sample, and the second binding agent specifically targeting all proliferating cells in the sample.

Each of the first and second binding agents may be an antibody or a biologically active fragment thereof. In certain preferred embodiments, the first binding agent targets a phosphorylated form of histone H3 and the second binding agent targets Ki-67.

In another embodiment, a kit for neoplasm prognosis includes a first cell cycle specific binding agent specifically targeting all mitotic cells in a sample; a second cell cycle specific binding agent specifically targeting all proliferating cells in a sample; one or more detection reagents for visualizing bound complexes indicative of mitotic and proliferative cells; and instructions for use. The first and second binding agents may be included in the same container or in separate containers.

The above described cocktail may be used in performing the various methods described herein. For example, one can use a cocktail/composition including both an antibody that specifically binds mitotic cells (e.g., an anti-PH3 antibody) and an antibody that specifically binds proliferating cells (e.g., an anti-Ki67 antibody), thus enabling the simultaneous detection of both types of target cells in the same defined portion of a sample (e.g., in the same field of view in paraffin-embedded tissue sections). Co-immunostaining the same sample or same portion of a sample (e.g., the same tissue) with both agents enables the observer to score both Ki67-positive and mitotic cell simultaneously. It also ensures that the same scale is used for scoring both the parameters. To facilitate simultaneous detection of mitotic and proliferating cells within the same portion of a sample, the agents targeting these cell types may be labeled to allow for distinct recognition (e.g., with two distinct colors etc.). For example, an alkaline phosphatase reaction produces a pink color when labeling Ki67, and a horseradish peroxidase reaction produces a brown color when labeling PH3. Preferably, the antibodies within a cocktail exhibit little cross-reactivity.

Processing of Tissue Samples and Methodology for Analysis

1. Patient Selection.

A wide variety of patients diagnosed with a neoplastic condition or suspected of having a neoplastic condition can benefit from the present methods.

2. Cell and Tissue Sources.

As noted above, the present application includes methods of assessing the prognosis for a patient who has been diagnosed with a neoplasm or cancer. These methods and others described herein may commence by providing a biological sample that is suspected of including neoplastic cells. The biological sample can be a cell sample, a tissue sample or a sample of biological fluids carrying cells, such as blood, urine, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Any cell or tumor cell type can serve as a cell or tissue sample for the inventive method, including those described above. Cells can originate from a variety of different sources, including the breast, prostrate, lung, brain, colon, bladder, kidney, cervix, testis, ovary, liver, pancreas, head and neck, anogenital tissue, adrenal gland, and blood. The present methods may be applied to any patient (e.g., a human of any age, gender, or ethnicity) who has been diagnosed with a neoplasm or cancer. This includes patients diagnosed with a breast cancer; a biliary tract cancer; a bladder cancer; a brain cancer (e.g., a glioblastomas or medulloblastomas); a cervical cancer; a choriocarcinoma; a colon cancer; an endometrial cancer; an esophageal cancer; a gastric cancer; a hematological neoplasm (e.g., acute lymphocytic leukemia or lymphoma, Hodgkin's disease, acute myelogenous leukemia, T-cell acute lymphoblastic leukemia/lymphoma, hairy cell leukemia, chronic lymphocytic leukemia, chronic myelogenous leukemia, multiple myeloma, or an adult T-cell leukemia/lymphoma); an intraepithelial neoplasm including Bowen's disease and Paget's disease; a liver cancer; a lung cancer; a neuroblastoma; a melanoma, an oral cancer including squamous cell carcinoma; an ovarian cancer including ovarian cancer arising from epithelial cells, stromal cells, germ cells and mesenchymal cells; a pancreatic cancer; a prostate cancer; a rectal cancer; a sarcoma, including angiosarcoma, gastrointestinal stromal tumors, leiomyosarcoma, rhabdomyosarcoma, liposarcoma, fibrosarcoma, and osteosarcoma; a renal cancer including renal cell carcinoma and Wilms tumor; a skin cancer including basal cell carcinoma and squamous cell cancer; a testicular cancer including germinal tumors such as seminoma, non-seminoma (teratomas, choriocarcinomas), stromal tumors, and germ cell tumors; and a thyroid cancer including thyroid adenocarcinoma and medullary carcinoma. Typically, the cell sample is derived from tumor tissue that was surgically removed from a human patient or other mammal.

It should be appreciated that a variety of different tumor types can arise in certain organs, which may differ with regard to, for example, their clinical and/or pathological features and/or the agents expressed. Tumors arising in a variety of different organs are discussed, for example, in the WHO Classification of Tumours series, 4th ed, or 3rd ed (Pathology and Genetics of Tumours series), by the International Agency for Research on Cancer (IARC), WHO Press, Geneva, Switzerland. In certain embodiments, the neoplasm or cancer may be one that is considered resistant to treatment (e.g., hormone resistant or chemotherapeutic resistant).

3. Biopsy Techniques.

A variety of biopsy techniques may be used to obtain a cell or tissue sample such as, but not limited to excisional (i.e., removal of an entire lesion) or incisional (i.e., where a portion or wedge of tissue is removed). In some cases, a fine-needle may be required to withdraw cellular material from a tissue mass using aspiration techniques (e.g., aspiration biopsy). Further, cell or tissue samples may be cells isolated from any cell suspension, body fluid samples, or cells dislodged from tumor by any other means.

4. Preparation of Tissue Samples.

In the present methods, normal, neoplastic and/or cancer tissue samples can be formalin-fixed paraffin-embedded or may be fresh-frozen in an OCT compound (such compounds are well-known in the art) and sectioned or fixed with methanol or any other appropriate fixative (such fixatives, processes and types are well-known in the art). Formalin-fixed, paraffin-embedded tissue must be subjected to de-paraffinization, peroxide quenching and antigen retrieval (e.g., heating under pressure in a citrate buffer) prior to the staining steps that allow visualization of centrosomes and nuclei within the sample.

5. Labeling and Detection of Target Cell Antigens or Target Cell Subpopulations.

When assessing the number of mitotic cells and/or the number of proliferating cells, one can use any method known in the art, including immunohistochemistry (by bright field or fluorescence) and flow cytometry (see, e.g., Vignon et al., PLoS ONE 8(7): e68425. doi:10.1371/journal.pone.0068425). Both fluorescence (direct and indirect) and immunohistochemical (IHC) staining methods may be employed for the purpose of staining mitotic cells, proliferating cells, centrosomes and/or DNA for visualization purposes.

For immunohistochemistry or immunofluorescence, the sample can be fresh frozen or "fixed" with a fixative such as formaldehyde or glutaraldehyde as described above. The fluorescence-based and/or immunohistochemical-based staining methods may employ any one of the variety of antibodies directed against mitosis specific markers, such as MPM-2 and phospho Histone H3 (PHH3); proliferation specific markers, such as Ki67; and centrosomal markers, such as γ-tubulin. For viewing the cells by immunofluorescence, the sample may be exposed to an agent (e.g., a primary or secondary antibody) that is conjugated to a chromophor (e.g., a fluorochrome or fluorophore). Thus, the secondary antibodies for detecting Ki67, MPM-2, PHH3 and γ-tubulin, may be conjugated to suitable chromophors, such as Alexa Fluor 555, Alexa Fluor 488, TRITC-conjugated, FITC-conjugated etc. Many of the steps of preparing and analyzing a sample can be automated and/or computer-aided.

In certain preferred embodiments, determination of M-to-P ratios employs the use of clinically-facile multicolor immunohistochemistry methods, where different colored detection labels distinguish between different target markers. This improves simplifies the detection process and improves the accuracy of patient risk-stratification.

In certain embodiments, an anti-pericentrin antibody may be used as the primary antibody for labelling centrosomes instead of anti-γ-tubulin antibody. In other embodiments, the primary antibody itself is conjugated to a fluorophore or quantum dots or an enzyme for enabling visualization. When using quantum dots, visualization of centrosomes and quantitation of CASs may be multiplexed with (or carried out simultaneously along with) visualization of other proteins in the same sample.

In certain embodiments, as an alternative to fluorescence-based detection of centrosomes, immunohistochemical (IHC) staining may be employed for imaging centrosomes. For example, an HRP-based detection system employing hematoxylin counterstain may be used for imaging centrosomes (as brown colored dots) using a brightfield imaging system with optical sections (i.e., z-stacks) followed by image deconvolution to enable software-assisted 3D volume rendering as further described below. Centrosome volume ranges may be determined from immunohistochemically stained normal tissues to aid in analysis of iCTRs and mCTRs in tumor tissues. Alternatively, an alkaline phosphatase-based detection system (producing red color instead of brown) may be used in place of the HRP-based system for IHC. In other embodiments, there could be variation in the primary antibody used for labelling centrosomes. For example, instead of using γ-tubulin, pericentrin may be used for labelling whole centrosomes.

6. Binding Agents and Antibodies.

In certain embodiments, cell samples may be stained with one or more antibodies, biologically active fragments thereof, and/or binding agents directed against mitosis-specific or proliferation-specific cell markers. Although the invention is not so limited, either the first and/or the second binding agent can be an antibody. As used herein, the term "antibody" encompasses monoclonal antibodies, polyclonal antibodies, multivalent antibodies, multispecific antibodies, single chain antibodies, human or humanized antibodies, and antibody fragments or other variants that retain the ability to specifically bind a target antigen. Antibodies used in the present application can be purchased commercially or, if necessary or desired, can be generated using techniques well known in the art. The same is true for any antibody useful in the context of the present methods (e.g., for antibodies that stain, label, or target mitotic cells, proliferating cells, pericentriolar matrix (PCM) etc.). (See, e.g., Antibodies: A Laboratory Manual (Second Edition), Edited by Edward A. Greenfield. 2014, Cold Spring Harbor Laboratory Press).

In certain preferred embodiments, the first binding agent binds to a mitotic specific marker. Exemplary mitosis specific markers include MPM-2 and phospho Histone H3 (PHH3). Exemplary mitosis specific binding agents include MPM-2 monoclonal antibody, anti-phospho Histone H3 antibody, Phospho-Histone H3 Ser28 (PHH3).

In other preferred embodiments, the second binding agent binds a proliferation-specific cell marker. Exemplary proliferation-specific markers include Ki-67, proliferating cell nuclear antigen (PCNA), Ki-S2, Ki-S5, MCM2, MCM3, MCM4, MCM5, MCM6, MCM7, MCM10, CAF-1 p60, CAF-1 p150, Pomfil2, Unc-53, CDC6, CDC7, CDC7 protein kinase, Dbf4, CDC14, CDC14 protein phosphatase, CDC45, topoisomerase 2 alpha, DNA polymerase delta, replication protein A (RPA), replication factor C (RFC) and FEN1. Anti-Ki-67 antibodies used in the present invention can be purchased commercially or, if necessary or desired, can be generated using techniques well known in the art.

As noted above, antibodies for use in the present invention can also be produced by injecting an antigen into laboratory or farm animals to evoke high expression levels of antigen-specific antibodies in the serum, which can then be removed from the animal. Polyclonal antibodies can be recovered directly from serum. Monoclonal antibodies can be produced by fusing antibody-secreting spleen cells from immunized mice with immortal myeloma cell to create monoclonal hybridoma cell lines that express the specific antibody in cell culture supernatant.

In certain embodiments, cell samples may be stained with one or more antibodies, biologically active fragments thereof, and/or binding agents directed against pericentriolar matrix components. Preferably, the primary antibody or binding agent specifically binds an antigen, protein or component of the pericentriolar matrix (PCM) that shows substantial localization to centrosomes at all stages of the cell cycle (i.e., interphase, mitosis (including prophase, metaphase, anaphase, telophase) and cytokinesis). In some embodiments, the primary antibody or binding agent is conjugated to a fluorophore or quantum dot or enzyme, etc. to facilitate visualization of signal. When using quantum dots, visualization of centrosomes and quantitation of CASs may be multiplexed with (or carried out simultaneously along with) visualization of other proteins in the same sample. In other embodiments, a secondary antibody or binding agent that binds to the primary antibody or binding agent is used to facilitate visualization. By colocalizing with centrosomes, the PCM binding agents produce a detectable signal above background so as to provide reliable image acquisition and 3D volume rendering. Volume rendering creates a binary image for volume determination.

Components of the PCM that localize to the PCM throughout the cell cycle include proteins include γ-tubulin, pericentrin, centromere protein J (CPAP/Sas-4) and ninein. Accordingly, these PCM components may be targeted using e.g., anti-γ-tubulin antibodies, including e.g., T3320, T-3195, T-3559, and C7604 (Sigma-Aldrich); ab11317, ab16504, ab27074 (Abcam); and sc-7396 (Santa Cruz Biotechnology); anti-pericentrin antibodies, including e.g., A301-348A, A301-349A and IHC-00264 (Bethyl Laboratories); ABT59 (EMD Millipore); ab4448, ab28144, ab99342, ab84542, ABIN968665, ABIN253211, ABIN253210, ABIN910327 (Abcam); CPBT-42894R1I, CPBT-42892RH, CPBT-42891RN (Creative BioMart); sc-28145, sc-28143, sc-28144, sc-68928 (Santa Cruz Biotechnology), HPA016820, HPA019887 (Sigma-Aldrich); NB100-61071, NBP100-61072, NBP1-87771 and NBP1-87772 and (Novus Biologicals); anti-centromere protein J antibodies, including e.g., ABIN527721, ABIN527722 and ABIN527723 (Abcam); 101-10278 (Ray-Biotech); and CABT-22656MH (Creative BioMart); and anti-ninein antibodies, including e.g., ab52473, ab4447 (Abcam); 41-3400 (Life Technologies); orb100831 (Biorbyt); HPA005939 (Atlas Antibodies); sc-376420 and sc-292089 (Santa Cruz Biotechnology).

Alternatively, or in addition, the antibodies or binding agents may target one or more of the following: the nucleus of a cell, comprised of key structural components such as the nuclear envelope, nucleoplasm, nucleoskeleton, nuclear lamina (including lamin proteins, such as LEM3), RNA molecules, chromosomes, chromatin, including euchromatin and heterochromatin, nucleolus, and other subnuclear bodies (e.g., Cajal bodies, Gemini of coiled bodies or gems, RAFA domains, polymorphic interphase karyosomal association (PIK), promyelocytic leukaemia (PML) bodies, paraspeckles, splicing speckles and perichromatin fibrils). In other embodiments, the antibody or binding agent is an antibody or binding agent that is capable of binding to any subcellular organelle that is present as one copy per cell or whose number of copies per cell is constant for a given cell cycle phase and is well-established.

In other embodiments, centriolar markers are used to stain centrioles and provide 3-dimensional information about centriolar volumes and structural aberrations.

Although the invention is not so limited, when any nuclear component or nuclear membrane component is targeted, the stain may be a fluorescent protein-based marker for the nucleus. Exemplary fluorescent protein-based nuclear markers include, but are not limited to CellLight Nucleus-Green Fluorescent Protein (C 10602), CellLight®Nucleus-RFG (Red Fluorescent Protein; 10603), CellLight®Nucleus-Cyan Fluorescent Protein and Alexa Fluor 488 conjugate of Histone H1 (H13188)); nuclear counterstains for live cells and unfixed tissues, such as Hoechst 33342 dye and SYTO dyes 40 (S11351), 11 (S7573), 13 (S7575), 12 (S7574), 14 (S7576), 16 (S7578), 17 (S7579) and 59 (511341)); nucleic acid stains, including dimeric cyanine dyes, and fluorescein-1 2-dUTP (C7604); 4',6-diamindino-2-phenylindole (DAPI; D1306, D3571, D21490); Hoechst stains, such as Hoechst 33258, Hoescht 34580, Hoechst S769121 (N21485) and Hoeshst 33342 (H1399, H3570 and H21492); BOBO-1 (B3582), BOBO-3 (B3586), SYTOX (S7020), SYTOX (Si 1368), SYTOX Blue (511348, S34857), YO-PRO-1 dye (Y3603), TOTO-1 (T3600), TOTO-3 (T3604), TO-PRO-3 (T3605), YOYQ-1 (Y3601), propidium iodide (P1304MP, P3566, P21493); and other chromosome banding dyes, including 7-aminoactinomycin D (7-AAD, A1310) and 9-amino-6chloro-2-methoxyacridine (ACMA, A1324).

Quantitating the Numeric and Structural Degree of Centrosome Amplification (CA)

As described above, the method may additionally include quantitating the numeric and structural degree of centrosome amplification (CA) in tumor samples as further described in U.S. patent application Ser. No. 14/632,778, filed Feb. 26, 2015, the disclosure of which is expressly incorporated by reference herein. A protocol for determining one or more CA scores (CAS) in normal, neoplastic and/or cancer cells using a standardized, quantitative method may be utilized in the methods described herein. This methodology involves a key transformative step of classifying centrosomes into individually distinguishable centrosomes (iCTRs) and megacentrosomes (mCTRs). Although these types of aberrations often occur together, their biological origin and clinical consequences may be different. These two different types of aberrations can make different contributions to the development and progression of neoplasms or cancer, hence the classification scheme herein facilitates quantitation of these types of aberrations separately.

iCTRs are centrosomes that stain positive for γ-tubulin, with centrosomes numbers and boundaries clearly distinguishable and volumes that lie within the range of centrosome volumes found in normal tissue (e.g., 0.23-0.76 cubic microns for breast tissue immunostained for γ-tubulin). mCTRs are centrosomes in a neoplastic region that stain positive for γ-tubulin and whose volume is greater than the upper limit of the centromere volume range found in corresponding normal tissue (e.g., 0.76 cubic micron for breast tissue immunostained for γ-tubulin). mCTRs could either be centrosomes with aberrantly large volumes or could represent a situation wherein multiple centrosomes are clumped together so closely that their precise numbers and boundaries cannot be discerned or resolved.

For each cell in a sample, a measure of the severity of centrosome amplification (numerical or structural) with reference to a normal centrosome numbers and volumes may be determined. In addition, for each sample, the frequency of numerical and structural amplification may be quantitated through calculation of CA score for iCTRs ($CAS_i$) and CA score for mCTRs ($CAS_m$), respectively. Scaling factors may be included in algorithms to ensure that $CAS_i$ and $CAS_m$ have the same weight in the cumulative CA score ($CAS_{total}$).

As used herein, the term "normal centrosomes" refers to centrosomes found in normal tissue (including adjacent non-involved tissue in a tumor core biopsy or resected tumor tissue) and stain positive for γ-tubulin, with numbers and boundaries clearly distinguishable and volume not exceeding the normal range of centrosomes of the corresponding tissue or cell type. For each tissue type, the normal range of centrosome volumes is determined from a large cohort of normal tissue samples. For example, centrosome volumes (as determined by immunostaining for γ-tubulin) in normal breast tissue range from 0.23 to 076 cubic microns; in normal pancreatic cell tissues from 0.20 to 0.56 cubic microns; and in normal bladder cell tissues from 0.35 to 0.74 cubic microns.

Generally, most normal somatic tissues average between 1-2 normal centrosomes per nucleus and no mCTRs. By contrast, cancer cells may have >2 iCTRs and several mCTRs per nucleus. Three-dimensional analysis of iCTRs and mCTRs in cancer cells can provide a useful tool for optimizing a risk profile of cancer in a patient to facilitate a more risk-adapted and optimal course of treatment.

In one embodiment, the method includes the step of processing a sample of neoplastic tissue from the patient to facilitate three dimensional visualization and demarcation of cell nuclei, iCTRs and mCTRs in a region of interest (ROI) defined by a plurality of cell nuclei. Three dimensional image data is generated so as to provide volume rendering of the iCTRs and mCTRs. In some embodiments, the 3D image is produced by confocal imaging of immunofluorescently stained centrosomes. In other embodiments, immunohistochemical (IHC) staining methods (e.g., HRP-based detection with hemotoxylin counterstain) are used to produce 3D image of centrosomes. Imaging of the centrosomes (brown colored dots) will be done using a bright field imaging system with optical sections (i.e., z-stacks) followed by image deconvolution, to enable software-assisted 3D volume rendering. Centrosome volume range as determined in the immunohistochemically stained normal tissues will be used to determine iCTRs and mCTRs in the tumor tissues. Images could either be obtained from 10-15 microscopic fields of view for each sample or by whole-slide imaging as long as optical sections are acquired for 3D volume rendering. For slides stained immunofluorescently for centrosomes, imaging is carried out in areas determined to be "tumor areas" based on comparison with a serial section stained with hematoxylin eosin (wherein tumor areas are pre-marked). In slides stained immunohistochemically for centrosomes, only iCTRs and mCTRs in tumor areas will be analyzed for CAS determination.

From this image data, the following are determined:
 (i) the number of iCTRs and mCTRs associated with each cell nucleus in the ROI,
 (ii) the volume of each iCTR and mCTR associated with each cell nucleus in the ROI,
 (iii) the average number of excess iCTRs (i.e., iCTRs in excess of 2) amongst cells that have >2 centrosomes; this gives a measure of the "severity" of numerical amplification present in the cells that bear numerically amplified centrosomes,
 (iv) the percentage of cell nuclei that have excess iCTRs (i.e., iCTRs in excess of 2); this gives a measure of the "frequency" or "prevalence" of numerical centrosome amplification,
 (v) the average volume deviation (compared to the upper limit of the volume of normal centrosomes) of mCTRs among the cells that bear mCTRs; this gives a measure of the "severity" of structural amplification present in cells that bear structurally amplified centrosomes or mCTRs,
 (vi) the percentage of cell nuclei that have mCTRs associated with them; this gives a measure of the "frequency" or "prevalence" of structural amplification of centrosomes.

Based on these numerical and structural determinations, one or more CASs are determined as further described below. The scores indicate the severity of centrosome amplification, the frequency of centrosome amplification, or both, in the sample and provide a measure of the level of risk associated with the neoplastic tissue.

Treatment with Antineoplastic Agents

The presently described methods provide a more accurate predictions of a patient's prognosis, including metastatic risk, and provide a more rational, efficacious basis for treatment. For example, in some embodiments, M:P ratio profiling of patients may help to decide which Luminal B patients should be given hormone therapy and chemotherapy (i.e., perhaps the higher-risk high cycling kinetics subclass) and who should receive hormone therapy alone. Further, when combined with determination of CAS scores, M:P ratios might help clinicians to decide who might benefit from declustering drugs and anti-mitotic therapeutics, including chemotherapeutic agents.

In some embodiments, M:P ratios can be used to predict who is more likely to benefit from specific types of neoadjuvant chemotherapy. In other embodiments, the M:P ratios can be used to stratify TNBCs into high cycling kinetics (higher-risk) who might require aggressive treatment and low cycling kinetics subclasses for whom less aggressive therapy may suffice.

In view of the foregoing, in certain embodiments, the patient is treated with at least one antineoplastic agent based on the results from the M:P determination. Exemplary antineoplastic agents include anti-mitotic agents, anti-interphase agents, anti-microtubule agents, anthracycline-based agents and aromatase inhibitor agents.

In certain embodiments, the patient is administered one or more centrosome declustering agents, including but not limited to griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, N2-benzyl-5-nitro-2-furamide, an anthracin compound as described in U.S. Patent Application Publication 2008/0051463; a 5-nitrofuran-2-carboxamide derivative as described in U.S. Provisional Application 61/619,780; and derivatives and analogs therefrom.

In another embodiment, the patient is administered an inhibitor of HSET, a key mediator of centrosome clustering. The inhibitor of HSET can be a small molecule drug or a nucleic acid-based therapeutic, such as an siRNA, an shRNA-encoded expression vector or an antisense oligonucleotide, whereby the inhibitor inhibits the activity and/or expression of HSET in the targeted cell. Alternatively, or in addition, the patient may be administered an inhibitor of a protein that is upregulated with HSET or inhibitors of other proteins implicated in centrosome clustering. HSET co-regulated product targets include, but are not limited to Npap60L, CAS, Prc1, Ki67, survivin, phospho-survivin, Hif1α, aurora kinase B, p-Bcl2, Mad1, Plk1, FoxM1, KPNA2, Aurora A and combinations thereof. In other embodiments, the patient is administered one or more agents that block the nuclear accumulation of HSET during interphase.

siRNAs are double-stranded RNAs that can be engineered to induce sequence-specific post-transcriptional gene silencing of mRNAs. Synthetically produced siRNAs structurally mimic the types of siRNAs normally processed in cells by the enzyme Dicer. siRNAs may be administered directly in their double-stranded form or they may be expressed from an expression vector is engineered to transcribe a short double-stranded hairpin-like RNA (shRNA) that is processed into a targeted siRNA inside the cell. Suitable expression vectors include viral vectors, plasmid vectors and the like and may be delivered to cells using two primary delivery schemes: viral-based delivery systems using viral vectors and non-viral based delivery systems using, for example, plasmid vectors. Exemplary viral vectors may include or be derived from an adenovirus, adeno-associated virus, herpesvirus, retrovirus, vaccinia virus, poliovirus, poxvirus, HIV virus, lentivirus, retrovirus, Sindbis and other RNA viruses and the like.

As used herein, the term "oligonucleotide" refers to a single stranded nucleic acid containing between about 15 to about 100 nucleotides. An antisense oligonucleotide comprises comprise a DNA backbone, RNA backbone, or chemical derivative thereof, which is designed to bind via complementary binding to an mRNA sense strand of a target gene (such as HSET) so as to promote RNase H activity, thereby leading to degradation of the mRNA. Preferably, the antisense oligonucleotide is chemically or structurally modified to promote nuclease stability and/or increased binding. The single stranded antisense oligonucleotide may be synthetically produced or it may be expressed from a suitable expression vector. In addition, the antisense oligonucleotide may be modified with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like.

In certain embodiments, the small molecule drug targets the motor domain of HSET and/or specifically binds to the HSET/microtubule binary complex so as to inhibit HSET's microtubule-stimulated and/or microtubule-independent ATPase activities. In a specific embodiment, the small molecule drug is AZ82 or CW069 or a therapeutically effective derivative, salt, enantiomer, or analog thereof.

AZ82 binds specifically to the KIFC1/microtubule (MT) binary complex and inhibits the MT-stimulated KIFC1 enzymatic activity in an ATP-competitive and MT-noncompetitive manner with a Ki of 0.043 µM. Treatment with AZ82 causes centrosome declustering in BT-549 breast cancer cells with amplified centrosomes.

Alternatively, or in addition, the patient may be administered a poly(ADP-ribose) polymerase (PARP) inhibitor, an inhibitor of the Ras/MAPK pathway, an inhibitor of the PI3K/AKT/mTOR pathway, an inhibitor of FoxM1, Hif1α, survivin, Aurora, Plk1 or a combination thereof. Exemplary PARP inhibitors include, but are not limited to olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof. Exemplary Ras/MAPK pathway agents include, but are not limited to MAP/ERK kinase (MEK) inhibitors, such as trametinib, selumetinib, cobimetinib, CI-1040, PD0325901, AS703026, 804987655, RO5068760, AZD6244, GSK1120212, TAK-733, U0126, MEK162, GDC-0973 and combinations thereof. Exemplary PI3K/AKT/mTOR pathway inhibitors include, but are not limited to everolimus, temsirolimus, GSK2126458, BEZ235, PIK90, PI103 and combinations thereof.

Other Prescribed Therapies.

Alternatively, or in addition to administering centrosome declustering drugs, HSET-targeted drugs, or others described above, a patient exhibiting high CA scores may be additionally treated with adjuvant chemotherapeutic agents to further reduce the risk of adverse events, such as metastasis, disease relapse, and poor survival. Adjuvant chemotherapies may include administration of cyclophosphamide, taxanes, such as docetaxel and paclitaxel; anthracyclines, such as epirubicin and doxorubicin; gemcitabine, cisplatin, fluorouracil, ixabepilone, capecitabine, epidermal growth factor receptor-targeting agents, and combinations thereof.

The appropriate dosage ("therapeutically effective amount") of the therapeutic agent(s) will depend, for example, on the severity and course of the breast cancer, the mode of administration, the bioavailability of the therapeutic agent(s), previous therap(ies), the age and weight of the patient, the patient's clinical history and response to the therapeutic agent(s), the type of the therapeutic agent used, discretion of the attending physician, etc. The therapeutic agent(s) are suitably administered to the patent at one time or over a series of treatments and may be administered to the patient at any time from diagnosis onwards. The therapeutic agent(s) may be administered as the sole treatment or in combination with other drugs or therapies useful in treating the breast cancer. When used with other drugs, the therapeutic agent(s) may be used at a lower dose to reduce toxicities and/or side effects.

The therapeutic agent(s) may be administered to the patient with known methods, such as intravenous administration as a bolus or by continuous infusion over a period of time, by intramuscular, intraperitoneal, intracerebrospinal, subcutaneous, intra-articular, intrasynovial, intrathecal, oral, topical and/or inhalation routes. As a general proposition, the therapeutically effective amount(s) of the above described therapeutic agent(s) will be in the range of about 1 ng/kg body weight/day to about 100 mg/kg body weight/day whether by one or more administrations. In a particular embodiments, each therapeutic agent is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In certain embodiments, the therapeutic agent(s) are administered at a dose of 500 µg to 20 g every three days, or 10 µg to 400 mg/kg body weight every three days. In other embodiments, each therapeutic agent is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The therapeutic agent(s) may be administered daily, or every 2, 3, 4, 5, 6 and 7 days, or every 1, 2, 3 or 4 weeks.

In other particular embodiments, the therapeutic agent(s) are administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage(s) will be dependent on the condition, size, age and condition of the patient.

Various alternatives (e.g., different types of cancers and types of reagents) may be utilized. It is to be understood that various combinations can be employed and any one or more of the listed alternatives can be excluded from the compositions of the invention.

EXAMPLES

Example 1—Materials and Methods for Analyzing Mitotic Cells and Proliferative Cells in the Same Field 1. Data-Mining.

Clinical records of 4342 breast cancer patients diagnosed between 2005 and 2009 were obtained from Northside Hospital, Atlanta. Histologic grading was performed by pathologists at Northside Hospital in accordance with Table 1. 2731 patients out of the total were excluded from this analysis due to missing information regarding KI, MI, hormone-receptor status or OS. Clinical records of the remaining 1611 patients who met all inclusion criteria were used for the analyses described below. Table 1 depicts the clinicopathologic characteristics of the breast cancer patient cohort analyzed in the Northside Hospital study.

The data mining was further extended to cover deidentified clinical records of 1492 breast cancer patients obtained from Nottingham University Hospital, UK (Table 2) and 1597 breast cancer patients obtained from Emory University Hospital, Atlanta (Table 3). The patients' clinicopathologic characteristics are described in Tables 2 and 3.

TABLE 1

Clinicopathologic characteristics of 1611 breast cancer patients from Northside Hospital.

| Factor | Status | Number of patients (Total n = 1611) | % out of total |
|---|---|---|---|
| ER | | | |
| | Positive | 1259 | 78.15 |
| | Negative | 339 | 21.04 |
| | Unknown | 13 | 0.81 |
| PR | | | |
| | Positive | 1086 | 67.41 |
| | Negative | 511 | 31.72 |
| | Unknown | 14 | 0.87 |
| HER2 | | | |
| | Positive | 1088 | 67.54 |
| | Negative | 520 | 32.28 |
| | Unknown | 3 | 0.19 |

TABLE 1-continued

Clinicopathologic characteristics of 1611 breast cancer patients from Northside Hospital.

| Factor | Status | Number of patients (Total n = 1611) | % out of total |
|---|---|---|---|
| Glandular differentiation Score | | | |
| | 1 | 171 | 10.61 |
| | 2 | 451 | 28.00 |
| | 3 | 989 | 61.39 |
| Nuclear Grade | | | |
| | 1 | 435 | 27.00 |
| | 2 | 728 | 45.19 |
| | 3 | 448 | 27.81 |
| Mitotic Score | | | |
| | 1 | 819 | 50.84 |
| | 2 | 472 | 29.30 |
| | 3 | 448 | 27.81 |
| Nottingham Grade | | | |
| | I | 539 | 33.46 |
| | II | 638 | 39.60 |
| | III | 434 | 26.94 |
| Subtype | | | |
| | ER/PR− Her2+ | 131 | 8.13 |
| | Luminal A | 584 | 36.25 |
| | Luminal B Her2+ | 384 | 23.84 |
| | Luminal B Her2− | 299 | 18.56 |
| | Triple Neg | 197 | 12.23 |
| | Unknown | 16 | 0.99 |
| Ki67 | | | |
| | <=15 | 848 | 52.64 |
| | <=30 | 317 | 19.68 |
| | >30 | 446 | 27.68 |
| Metastasis Status | | | |
| | Local Relapse | 27 | 1.68 |
| | Distant | 23 | 1.43 |
| | None | 1064 | 66.05 |
| | Unknown | 547 | 33.95 |
| Race | | | |
| | European-American | 1290 | 80.07 |
| | African-American | 210 | 13.04 |
| | Other | 111 | 6.89 |
| Sex | | | |
| | Female | 1606 | 99.69 |
| | Male | 4 | 0.25 |
| | Unknown | 1 | 0.06 |
| Age | | | |
| | <50 | 539 | 33.46 |
| | 50-69 | 837 | 51.96 |
| | 70-75 | 219 | 13.59 |
| | >75 | 10 | 0.99 |
| Median Follow up time | 1783 days | | |
| Median Age | 56 | | |

TABLE 2

Clinicopathologic characteristics of 1492 breast cancer patients from Nottingham University Hospita, UK.

| Factor | Status | Number of patients (Total n = 1492) | % out of total |
|---|---|---|---|
| ER | | | |
| | Negative | 376 | 25.3 |
| | Positive | 1109 | 74.7 |
| | Missing | 7 | — |
| PR | | | |
| | Negative | 582 | 40.4 |
| | Positive | 857 | 59.6 |
| | Missing | 53 | — |
| HER2 | | | |
| | Negative | 1249 | 87.2 |
| | Positive | 182 | 12.7 |
| | Unknown | 1 | 0.1 |
| | Missing | 60 | — |
| Mitotic Score | | | |
| | 1 | 543 | 36.4 |
| | 2 | 278 | 18.6 |
| | 3 | 671 | 45.0 |
| Nuclear Grade | | | 2.4 |
| | 1 | 36 | |
| | 2 | 575 | 38.5 |
| | 3 | 881 | 59.0 |
| Nottingham Grade | | | |
| | 1 | 225 | 17.1 |
| | 2 | 490 | 32.8 |
| | 3 | 747 | 50.1 |
| Subtype | | | |
| | HER2+ | 85 | 6.0 |
| | Luminal A | 577 | 40.8 |
| | Luminal B | 499 | 35.3 |
| | Triple Negative | 254 | 18.0 |
| | Missing | 77 | — |
| Ki67 | | | |
| | <=15 | 741 | 49.7 |
| | 16-30 | 205 | 13.7 |
| | >30 | 546 | 36.6 |
| Metastasis Status | | | |
| | None | 979 | 66.0 |
| | Distant | 505 | 34.0 |
| | Unknown | 8 | — |
| Age | | | |
| | <50 | 497 | 33.3 |
| | 50-69 | 955 | 64.0 |
| | 70-75 | 40 | 2.7 |
| Tubule Formation | | | |
| | 1 | 93 | 6.2 |
| | 2 | 493 | 33.0 |
| | 3 | 906 | 60.7 |

TABLE 3

Clinicopathological characteristics of 1597 breast cancer patients from Emory University Hospital, Atlanta.

| Factor | Status | Number of patients (Total n = 1597) | % out of total |
|---|---|---|---|
| ER | | | |
| | Negative | 336 | 21.0 |
| | Positive | 1261 | 79.0 |

TABLE 3-continued

Clinicopathological characteristics of 1597 breast cancer patients from Emory University Hospital, Atlanta.

| Factor | Status | Number of patients (Total n = 1597) | % out of total |
|---|---|---|---|
| PR | | | |
| | Negative | 563 | 35.3 |
| | Positive | 1030 | 64.7 |
| | Missing | 4 | — |
| HER2 | | | |
| | 0 | 1384 | 86.7 |
| | Positive | 213 | 13.3 |
| Mitotic Score | | | |
| | 1 | 925 | 58.0 |
| | 2 | 398 | 25.0 |
| | 3 | 272 | 17.1 |
| | Missing | 2 | — |
| Nuclear Grade | | | |
| | 1 | 175 | 11.0 |
| | 2 | 731 | 45.9 |
| | 3 | 687 | 43.1 |
| | Missing | 4 | — |
| Nottingham Grade | | | |
| | 1 | 411 | 26.0 |
| | 2 | 725 | 45.9 |
| | 3 | 444 | 28.1 |
| | Missing | 17 | — |
| Subtype | | | |
| | HER2+ | 64 | 4.0 |
| | Luminal A | 463 | 29.0 |
| | Luminal B | 828 | 51.8 |
| | Triple Negative | 242 | 15.2 |
| Ki67 | | | |
| | <=15 | 575 | 36.0 |
| | 16-30 | 301 | 18.8 |
| | >30 | 721 | 45.1 |
| Metastasis Status | | | |
| | Distant | 4 | 0.30 |
| | None | 679 | 42.52 |
| | Unknown | 914 | 57.2 |
| Race | | | |
| | Black | 758 | 48.2 |
| | White | 758 | 48.2 |
| | Others | 56 | 3.51 |
| | Missing | 25 | — |
| Sex | | | |
| | Female | 707 | 98.5 |
| | Male | 11 | 1.5 |
| | Unknown | 879 | — |
| Age | | | |
| | <50 | 431 | 27.0 |
| | 50-69 | 883 | 55.3 |
| | 70-75 | 130 | 8.1 |
| | >75 | 153 | 9.6 |
| Tubule Formation | | | |
| | 1 | 158 | 9.9 |
| | 2 | 463 | 29.0 |
| | 3 | 973 | 61.0 |
| | Missing | 3 | — |

2. KAMS Ratio Determination.

To compare MI, a categorical variable, based on mitotic score (i.e., 1, 2 or 3) to KI, a continuous variable expressed as a percentage, MI was converted to a percentage as follows. Briefly, 10 HPFs were evaluated in at least 5 patient samples, where on average, 10 HPFs were found to have ~500 cells. For patients with mitotic scores 1 and 2, mitotic cell counts were assumed to have values of 3.5 and 11 (average cell count value of those score ranges), respectively. For patients with a mitotic score of 3, a mitotic cell count of 15 (which is the floor value for mitotic score 3 category) was assumed. These mitotic cell counts provided an estimate of the number of mitotic cells per 500 cells (10 HPFs), thus providing the percentage of cells undergoing mitosis. The KAMS ratio for each patient was calculated simply as a quotient of percent mitotic cells divided by percent Ki67-positive cells.

3. Statistical Analysis.

Differences among baseline results were established using a one-way analysis of variance (ANOVA) alongside a post-hoc Tukeys range test. Survival curves were obtained via the Kaplan-Meier method with significance determined using the log-rank test. Survival time was measured from the initial diagnosis to either an event (death) or to the final follow up (censor) and was thus an indicator of overall survival (OS). Progression-free survival (PFS) is calculated as the time interval from first diagnosis to date of first local recurrence in the absence of metastasis or metastasis in the absence of local recurrence or death (if that occurred without recurrence or metastasis). Breast cancer-specific survival (BCSS) was calculated as the time from first diagnosis to death from breast cancer. To obtain hazard ratios and the fit statistics, a Cox proportional hazard model was employed. For categorical variables, the lowest risk-group was used as the reference to that parameter's hazard. For ideal thresholds, the FINDCUT macro developed by Jayawant N. Mandrekar et al. from Mayo Clinic (http://www2.sas.com/proceedings/sugi28/261-28.pdf) was used, which identifies the optimal cut-off point for continuous variables (i.e., M:P ratio) that predicts time to event outcomes. Using a macro by Mithat Gönen (% c-index), a concordance index (c-index) was determined for these models with censored outcomes. In order to determine if c-indices of multiple models were significantly different, a 100× bootstrap method was utilized where the model was trained on 60% of the samples and validated on the remaining 40% of the samples. The mean c-indices could then be compared using a student t-test.

To assess degree of agreement between pathologists for mitosis identification using either phoshpho-histone H3 (p-H3) or H&E staining, the intraclass correlation test (ICC) was employed using a macro developed by Li Lu and Nawar Shara (http://www.lexjansen.com/nesug/nesug07/sa/sa13.pdf). The average change in mitotic count determined using the two methods was compared via a t-test. All relevant tests were two-sided and used a significance level alpha of 0.05. All statistical analysis was done in either SAS or in Microsoft Excel.

4. Immunofluorescent Staining on Tissue Sections.

Formalin-fixed, paraffin-embedded tissue sections were incubated at 60° C.-70° C. for 2 h, followed by 2 xylene washes (5 min each) and sequential ethanol washes (100%, 95%, 70% and 50%). Antigen retrieval was carried out in citric acid buffer (pH 6.0) at 98° C. for 20 min. Slides were allowed to cool down and blocked in 5% BSA/PBS (30 min). Tissue sections were then incubated for 1 h with a cocktail of rat anti-human p-H3 antibody (1:500) (Abcam, Cambridge, UK) and mouse anti-human DM1A (α-tubulin, 1:1000) (Sigma-Aldrich, Mo., USA) followed by donkey anti-rat Alexa 488 (1:2000) and goat anti-mouse Cy5 (1:2000) (Invitrogen, Grand Island, N.Y.) secondary antibody incubation for 1 h. Slides were then washed 3 times in PBS followed by 1 h incubation with rabbit anti-human Ki67 (1:1000) (Abcam, Cambridge, UK) and goat antirabbit Alexa 405 (Invitrogen, 1:2000) secondary antibody incubation for 1 h. Slides were again washed 3 times in PBS followed by incubation with Propidium Iodide (0.1 ug/ml) for 15 min and washing in PBS. Finally, coverslips were mounted on the slides using Prolong Antifade mounting medium (Invitrogen, Grand Island, N.Y.). Ziess LSM 700 confocal microscope was used to capture immunofluorescence images at 63× objective magnification.

Paraffin-embedded slides were processed as described in the immunofluorescent staining section. Following antigen retrieval, peroxide quenching was done in 5% H2O2 solution for 30 min and the slides were blocked in 5% BSA/PBS (30 min) Tissue sections were then incubated for 1 h with rabbit-human p-H3 antibody (1:500) (Abcam, Cambridge, UK). Peroxide-based antibody detection kit was used (Universal LSAB™+Kit/HRP) (Dako, Golstrup, Denmark) to develop brown color. Slides were then counterstained with Haematoxylin (Fisher Scientific, Waltham, Mass.) for 5 min followed by 3H$_2$O washes. For H&E staining, slides were directly stained with Hematoxylin (5 min incubation) after tissue rehydration. Slides were then dipped in acid alcohol followed by ammonia water and then stained with Eosin Y (1 min incubation) (Fisher Scientific, Waltham, Mass.). After 3H$_2$O washes, all tissues were then dehydrated in sequential ethanol washes (50%, 70%, 95%, 100%) followed by 3 xylene washes. Coverslips were mounted using toluene-based mounting medium (Secure Mount, Fisher Scientific, Waltham, Mass.).

5. Representative Protocol for Double-Color Immunohistochemistry

1. Put slides in the oven at 67° C. for 2 hours.
2. Put slides in a slide holder and perform each step in the following order. Put in Xylene three times five minutes each.
3. Quench endogenous hydrogen peroxide activity for 45 minutes by placing slides in: 95 ml MeOH, 5 ml hydrogen peroxide (30% by vol)
4. Put slides in a sequential order in 100%, 95%, 70%, and 50% EtOH, 5 minutes each.
5. Prepare citrate buffer: 210 mg citrate in 100 ml pure water and add two drops Triton X-100.
6. Preheat pressure cooker. Put slides in citric acid solution and pressure cook for 10 minutes at 125° C. Let it cool down (will take another 20-30 minutes).
7. Put slides in ice for 30 minutes to cool down to room temperature.
8. Put slides in TBST 2×5 minutes.
9. Block slides using antibody diluents and blocker (BioGenex, # QA900-91, LOT QA9000807) for one hour at room temperature.
10. Gently dry area around the sections and draw a line with a liquid blocker pen to prevent spillage of antibody. Prepare rat anti-human phospho-Histone H3 (PH3) antibody [Abcam, #ab10543, LOT GR1054868] at a dilution of 1:1000 with BioGenex blocker.
11. Incubate slides with primary antibody overnight at 4° C.
12. Tap off antibody and wash three times with TBST 5 minutes for each wash.
13. Put Polyclonal Dako Rabbit anti-Rat Immunoglubulins/HRP (# P0450, LOT 00082902) for one hour.
14. Incubate with substrate-chromogen solution until brown color develops with Dako Kit (1-2 minutes). 1 ml DAB substrate [LOT 10081846]+1 drop chromogen [LOT 10081846], use immediately.
15. Rinse gently with water and let the slides stay in water for two minutes.
16. Block the slides with 5% BSA in PBS+0.05% Triton X-100.
17. Prepare rabbit anti-human Ki67 antibody (Abcam, #ab16667, LOT GR 1054868) at a dilution of 1:1000.
18. Incubate slides with Ki67 primary antibody overnight 4° C.
19. Tap off antibody and wash three times with TBST for 5 minutes each.
20. Put Linker for Alkaline Phosphatase (Biogenex, QA900-91, LOT HK3310307) for 35 minutes.
21. Wash slides with TBST three times for 5 minutes each.
22. From SIGMA Alkaline Phosphatase Magenta kit (# AM0100-1KT), mix 20 ul liquid substrate initiator from the [LOT 026K1143] and 20 ul SIGMA Alkaline Phosphatase Magenta liquid for two minutes and put SIGMA 1 ml Alkaline Phosphatase Magenta liquid substrate buffer [LOT 026K1144].
23. Incubate with substrate-chromogen solution until red color develops (~10 minutes).
24. Rinse with water. While slide is still wet, counterstain with hematoxylin (EMD, #65067-75) for 1.5 min.
25. Rinse until slide runs clear.
26. Put slides sequentially in 50%, 70%, 95% and 100% EtOH for 5 minutes each.
27. Put slides in Xylene three times for 5 minutes each in the fume hood.
28. Add mounting medium (Secure Mount, Protocol, #022-208) to slide while still moist from Xylene, and add coverslip. Let dry in the fume hood and put transparent nail polish around the cover slip.

Example 2—Quantification of Mitotic Figures from H&E-Stained Slides Underestimates Mitotic Population KI and MI are normally determined by pathologists in different tissue sections and evaluated on disparate scales, which: (i) overlook the fact that mitotic cells comprise a subset of cycling cells; (ii) make a direct cell-matched comparison of KI and MI impossible (FIG. 1, Panel A) and (iii) preclude evaluation of mitotic propensity and cell-cycling kinetics of the proliferative population in a tumor. Evidence provided herein suggests that the proportion of mitotic cells amongst the proliferative population within a tumor provides a measure of the risk associated with the tumor due to erroneous mitoses. This "dangerous" fraction of proliferating cells can be quantitated with a high degree of accuracy by simultaneous visualization of both mitotic and Ki67-positive cells in the same field (FIG. 1, Panel A).

A commonly used marker to identify M-phase cells is p-H3. In order to assess the value of p-H3 for determining mitotic score by immunocytochemistry, 45 paraffin-embedded breast tumor sections were stained with either H&E or anti-p-H3 antibody. Three pathologists determined mitotic scores based on H&E and p-H3 for the same pre-marked areas in the two sets of slides in a blinded manner (FIG. 1, Panel B). Higher and more reproducible mitotic scores resulted when mitotic cells were counted in p-H3-stained slides vs. H&E stained sections (FIG. 1, Panel Ci). Average mitotic scores via p-H3 staining were higher by an average of 46.6% (p<0.0001) (FIG. 1, Panel Ci). The better contrast in p-H3 and easier recognition of mitotic figures enabled more rapid determination of mitotic scores in p-H3-stained slides (FIG., Panel Cii), as the average time spent scoring p-H3 slides was ~37% lower than for H&E slides.

Next, an Intraclass correlation coefficient (ICC) was used to assess consistency of measurements made by the three pathologists. There was a significant increase in agreement among the three pathologists when evaluating mitotic scores using p-H3 staining (ICC=0.57) compared to mitotic scores using H&E staining (ICC=0.38) (p<0.05). These data underscore that p-H3 stain significantly increases inter-observer reproducibility than H&E in evaluation of MI.

Example 3—Integration of KI and MI Enhances Patient Risk-Stratification

FIG. 2. Panel Ai depicts Kaplan-Meier survival plots (Breast cancer-specific survival) showing stratification of Lum B patients (n=495) from the Nottingham University dataset based on an ideal threshold (KAMS threshold=0.375). Panel Aii shows the tests of equality of the survival function over strata, which indicate that the survival difference between the groups is statistically significant. Panel Aiii shows the summary of the number of censored and uncensored values in the survival analysis of Lum B patients. Panel Bi depicts Kaplan-Meier survival plots showing stratification of TNBC patients (n=250) from the Nottingham University dataset based on an ideal threshold (KAMS threshold=0.413). Panel Bii shows the tests of equality of the survival function over strata, which indicate that the survival difference between the groups is statistically significant. Panel Biii shows the summary of the number of censored and uncensored values in the survival analysis of TNBC patients. Note that above threshold Lum B and TNBC patients show poorer prognosis.

FIG. 3. Panel Ai depicts Kaplan-Meier survival plots (Progression-free survival) showing stratification of a combined set of Lum B and TNBC patients (n=1070) from the Emory University dataset, based on an ideal threshold (KAMS threshold=0.111). Panel Aii shows the tests of equality of the survival function over strata, which indicate that the survival difference between the groups is statistically significant. Panel Aiii shows the summary of the number of censored and uncensored values in the survival analysis of the patient cohort. Note that above threshold Lum B and TNBC patients show poorer prognosis.

FIG. 4. Panel Ai depicts Kaplan-Meier survival plots (Overall survival) showing stratification of a combined set of Lum B and TNBC patients (n=880) from the Northside Hospital dataset, based on an ideal threshold (KAMS threshold=0.318). Panel Aii shows the tests of equality of the survival function over strata, which indicate that the survival difference between the groups is statistically significant. Panel Aiii shows the summary of the number of censored and uncensored values in the survival analysis of the Northside Hospital Lum B and TNBC patients. Note that above threshold Lum B and TNBC patients show poorer prognosis.

Figure 5:
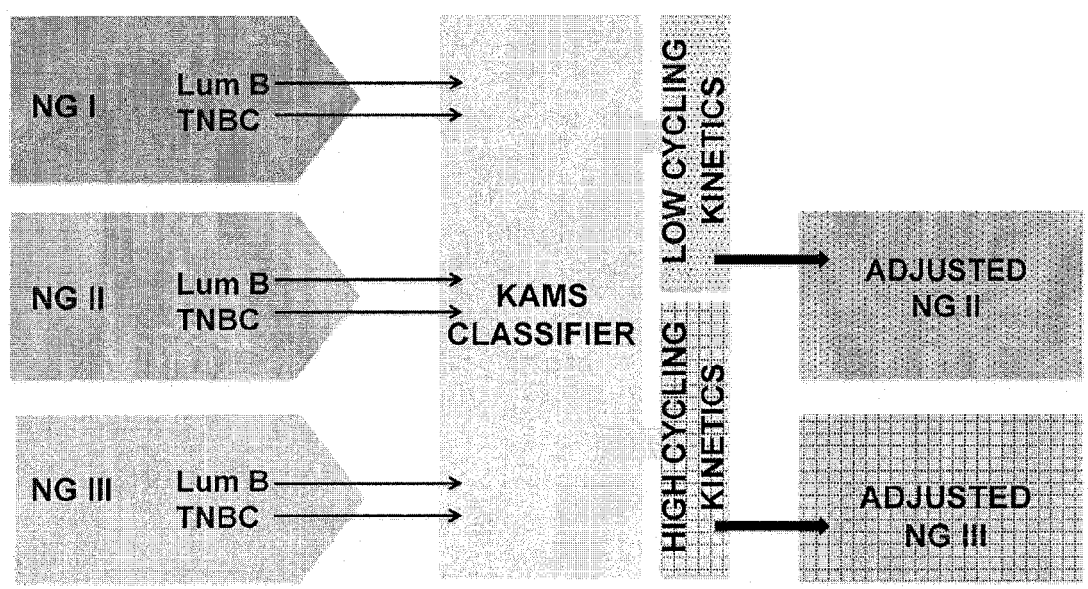
FIG. 5 depicts a patient grade-adjustment model, which creates an adjusted Nottingham Grade based on KAMS values of Lum B and TNBC patients.

FIG. 5 depicts a patient grade-adjustment model, which creates an adjusted Nottingham Grade based on KAMS values of Lum B and TNBC patients. This histological grade-adjustment model was then tested to see if incorporation of KAMS-classifier subsequent to conventional Nottingham classification would improve stratification of patients. In this model, all Lum A patients originally in NG III were adjusted into the "Adjusted NGII" category owing to their relatively good prognosis (this adjustment is not depicted in FIG. 5 since these patients represent <5% of the total cohort). All the Lum B and TNBC patients were then categorized by the KAMS classifier into a low-KAMS (low cell cycling kinetics) subclass and a high-KAMS (high cell cycling kinetics) subclass based on an ideal threshold. The "low cycling kinetics" subclass was then combined with the remainder of patients from the original NG II to generate the "Adjusted NG II" cohort. The "high cycling kinetics" subclass was then combined with the remainder of patients from the original NG III to generate the "Adjusted NG III" cohort.

FIG. 6 shows the histological grades of 1455 patients from the Nottingham University dataset (for whom progression-free survival data was available) were adjusted according to the grade adjustment model depicted in FIG. 5. Panel Ai depicts the Kaplan-Meier survival plot (Progression-free survival) of patients stratified by the original Nottingham Grading System. Panel Aii shows the tests of equality of the survival functions over strata, which indicate that the survival differences between the groups are statistically significant. Panel Aiii shows the summary of the number of censored and uncensored values for each Nottingham Grade in the survival analysis of the Nottingham University patients classified by the original Nottingham Grading System. Panel Bi depicts the Kaplan-Meier survival plot (Progression-free survival) of the Nottingham University patients after they were stratified and re-classified using the KAMS-classifier, thus yielding the "Adjusted NG I, II and III". The adjusted grading system boasts a better separation between PFS of the adjusted grades. Panel Bii shows the tests of equality of the survival functions over strata, which indicate that the survival differences between the Adjusted Nottingham Grades are statistically significant. Panel Biii shows the summary of the number of censored and uncensored values for each Adjusted Nottingham Grade in the survival analysis of the Nottingham University patients. Panel C shows a comparison of the model fit statistics, hazard ratios and concordance indices for the original and KAMS classifier-adjusted Nottingham Grades. Panel C shows a decrease of all 3 model-fit statistics (−2 log L, Akaike Information Criterion or AIC, and Schwarz Bayesian Criterion or SBC) for the adjusted model alongside an increase in hazard ratios (using NG I as the reference point for both models) both indicating the superior fit of the adjusted model, improved patient stratification and more accurate risk-segmentation of patients using the KAMS-classifier. A comparison of mean c-index (c-index is a measure of concordance for time-to-event data, in which increasing values between 0.5 and 1.0 indicate improved concordance between predicted and actual outcomes) of 100 bootstraps of the dataset (using 60% cases as training set and 40% cases as validation set), between the original NGS and KAMS-adjusted system shows comparable c-index for original and adjusted grading systems. Analysis of distribution of various breast cancer subtypes among the patient-cohort prior to (Panel Di) and after the KAMS-based grade reassignment (Panel Dii) shows the ability of this metric to distinguish between high- and low-risk breast cancer subtypes as the proportion of Lum B patients in the adjusted NG III is higher than in the original NG III. Moreover, this metric allowed the identification of lower-risk TNBC patients who moved from the original NG III into the adjusted NG II.

FIG. 7 shows the histological grades of 1460 patients from the Nottingham University dataset (for whom breast cancer-specific survival data was available) were adjusted according to the grade adjustment model depicted in FIG. 5. Panel Ai depicts the Kaplan-Meier survival plot (breast cancer-specific survival) of patients stratified by the original Nottingham Grading System. Panel Aii shows the tests of equality of the survival functions over strata, which indicate that the survival differences between the groups are statistically significant. Panel Aiii shows the summary of the number of censored and uncensored values for each Nottingham Grade in the survival analysis of the Nottingham University patients classified by the original Nottingham Grading System. Panel Bi depicts the Kaplan-Meier survival plot (breast cancer-specific survival) of the Nottingham University patients after they were stratified and re-classified using the KAMS-classifier, thus yielding the "Adjusted NG I, II and III". The adjusted grading system boasts a better separation between BCSS of the adjusted grades. Panel Bii shows the tests of equality of the survival functions over strata, which indicate that the survival differences between the Adjusted Nottingham Grades are statistically significant. Panel Biii shows the summary of the number of censored and uncensored values for each Adjusted Nottingham Grade in the survival analysis of the Nottingham University patients. Panel C shows a comparison of the model fit statistics, hazard ratios and concordance indices for the original and KAMS classifier-adjusted Nottingham Grades. Panel C shows a decrease of all 3 model-fit statistics (−2 log L, Akaike Information Criterion or AIC, and Schwarz Bayesian Criterion or SBC) for the adjusted model, alongside an increase in hazard ratios (using NG I as the reference point for both models) both indicating the superior fit of the adjusted model, improved patient stratification and more accurate risk-segmentation of patients using the KAMS-classifier. A comparison of mean c-index (c-index is a measure of concordance for time-to-event data, in which increasing values between 0.5 and 1.0 indicate improved concordance between predicted and actual outcomes) of 100 bootstraps of the dataset (using 60% cases as training set and 40% cases as validation set), between the original NGS and KAMS-adjusted system shows comparable c-index for original and adjusted grading systems. Analysis of distribution of various breast cancer subtypes among the patient-cohort prior to (Panel Di) and after the KAMS-based grade reassignment (Panel Dii) clearly shows the ability of this metric to distinguish between high- and low-risk breast cancer subtypes as the proportion of Lum B patients in the adjusted NG III is higher than in the original NG III. Moreover, this metric allowed the identification of lower-risk TNBC patients who moved from the original NG III into the adjusted NG II.

FIG. 8, Panels A, B and C depict the mean KAMS values of Lum A and Lum B patients in NG I, NG II and NG III, respectively, in a combined dataset comprising patients from Northside Hospital, Atlanta, Emory University Hospital, Atlanta and Nottingham University Hospital, UK. Within each Nottingham Grade, the difference in the mean KAMS of Lum A and Lum B patients is statistically significant ($p<0.0001$).

Figure 9:
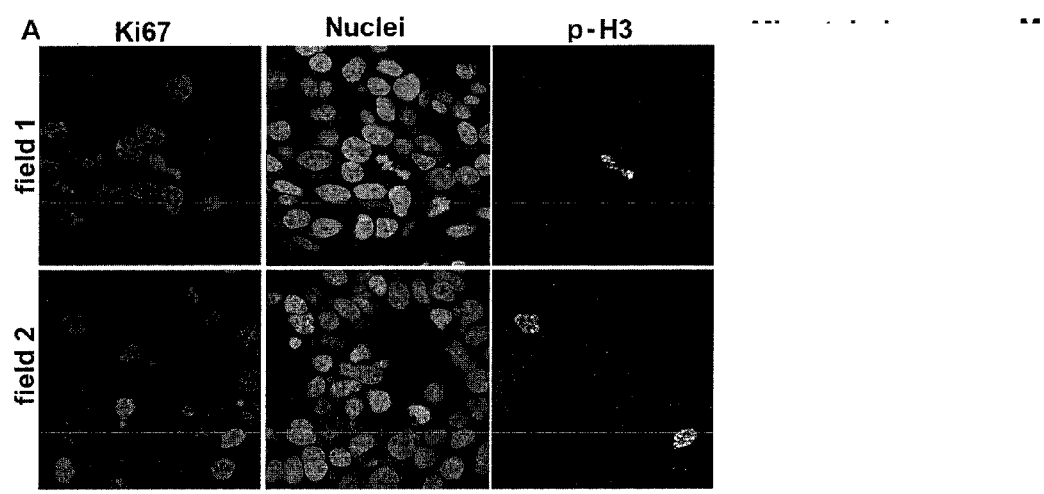
FIG. 9 depicts the extraction and integration of KI and MI from the same microscopic field using immunofluorescence microscopy.

FIG. 9 depicts the extraction and integration of KI and MI from the same microscopic field using immunofluorescence microscopy. Field 1 and 2 show different fields depicting mitotic propensities observed in two breast tumors immunostained for Ki67, p-H3, α-tubulin and DNA (Propidium Iodide). Sample in top row has 13 Ki67-positive cells, 1 p-H3-positive cells in a field, M-to-P ratio for field $1=1/13\times 100=7.69$. Sample in bottom row has 13 Ki67-positive cells, 2 p-H3-positive cells, M-to-P ratio for field $2=2/13\times 100=15.3$.

FIG. 10 depicts the extraction and integration of KI and MI to derive M-to-P Ratio from the same microscopic field using dual antibody immunohistochemistry. The antibodies used were directed against Ki67 and p-H3 and nuclei were visualized using hematoxylin.

Figure 11:
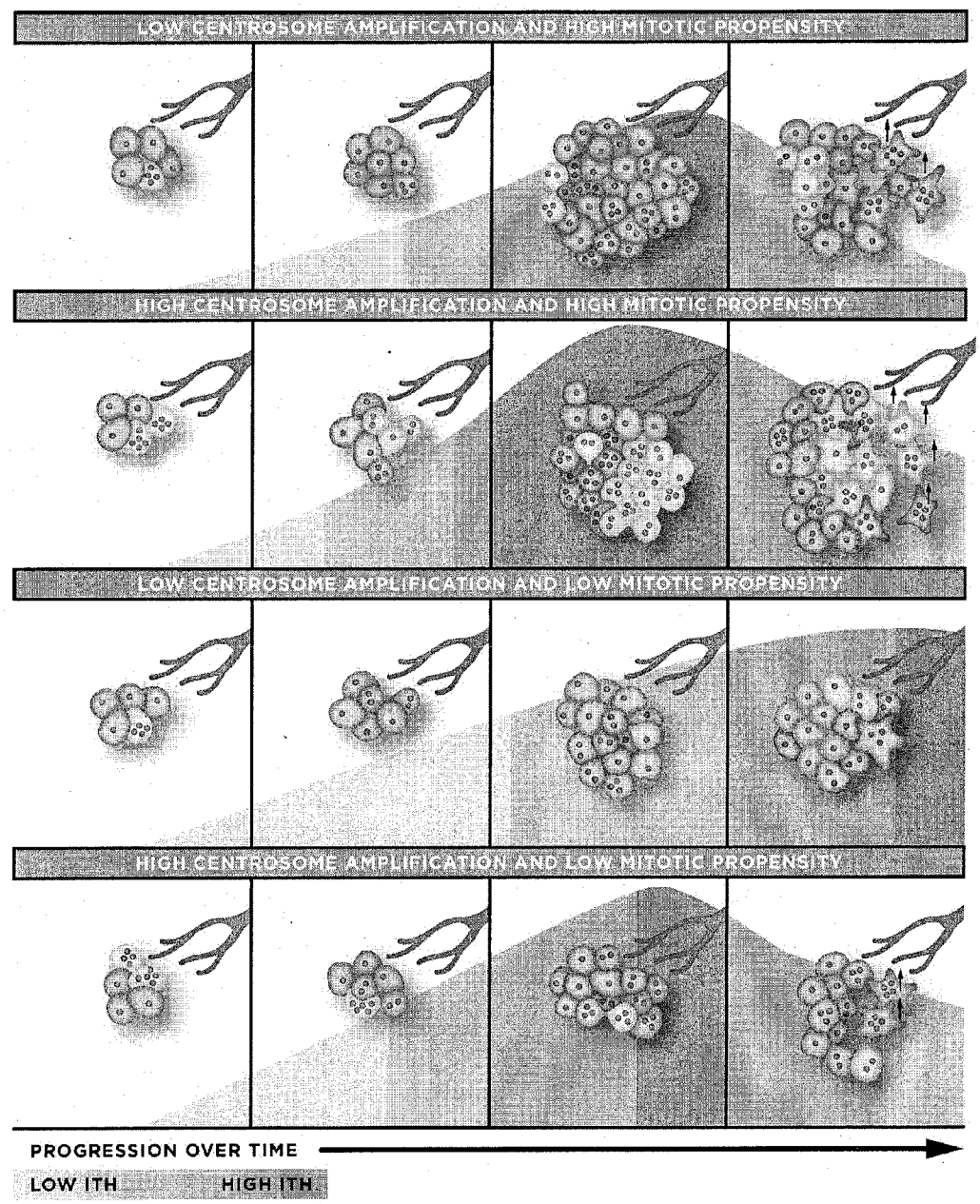
FIG. 11 depicts how the extent of centrosome amplification and inherent mitotic propensity (i.e., the M:P ratio) determine the rate at which intratumoral heterogeneity (ITH) is generated.

FIG. 11 depicts how the extent of centrosome amplification and inherent mitotic propensity (i.e., the M-to-P Ratio) determine the rate at which intratumoral heterogeneity (ITH) is generated. Centrosomes are depicted as small circles within the cell. This schematic describes how a tumor cell population (with different degrees of centrosome amplification and mitotic propensity) in the vicinity of a blood vessel evolves over time. This tumor cell population could represent either an entire primary tumor, an individual clone within a primary tumor, or a metastatic tumor evolving in parallel with a primary tumor in another location. Four scenarios are illustrated for this population which is at a very early stage in its lifetime: Rows 1 and 2-evolution of ITH when two cell populations with similarly high mitotic propensity start off with either low or high levels of centrosome amplification, respectively. Rows 3 and 4-evolution of ITH when two cell populations with similarly low mitotic propensity start off with either low or high levels of centrosome amplification, respectively. Each row has 4 panels depicting sequential snapshots of tumor population over time. ITH level of the tumor population is represented by the histogram in the background, the color of the histogram representing the level/degree of ITH at a particular time/stage in tumor evolution. The height of the histogram depicts the maximum level of ITH attained in each of the four scenarios. Variety of clones produced is represented by the number of differently colored cells. The rate of ITH is depicted by the variety of clones produced, tumor size and time it took the tumor to reach ITH peak which demarcates the switch in tumor agenda from mitosis to metastasis. Metastasis (if any) is depicted by black arrows pointing towards the blood vessel in the final panel in each row. Highest risk of metastasis occurs when both centrosome amplification levels and inherent mitotic propensity are high (Row 2).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method of assessing the prognosis for a patient who has been diagnosed with, or is suspected to have, a neoplasm, the method comprising:
    (a) exposing cells derived from a neoplastic tissue sample from the patient to two binding agents under conditions sufficient to allow the binding agents to bind preselected markers within the cells, wherein a first binding agent specifically targets mitotic cells and a second agent specifically targets proliferating cells;
    (b) exposing the cells in step (a) to detection reagents suitable for visualizing and discriminating between proliferating cells that are mitotic and proliferating cells that are non-mitotic;
    (c) determining the ratio of mitotic cells to proliferating cells (M:P ratio);
    (d) providing a prognosis based on the M:P ratio and the type of neoplasm,
    (e) processing a neoplastic tissue sample or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei, wherein the neoplastic tissue sample can be the same sample in step (a) or a different sample from the sample in step (a);

(f) determining the numbers of iCTRs and mCTRs associated with each cell nucleus in the ROI;

(g) determining the volume of each iCTR and mCTR in the ROI; and (h) calculating one or more centrosome amplification scores (CASs) values for the sample based on steps (f) and (g), wherein the neoplasm is Luminal B subtype breast cancer or triple negative breast cancer (TNBC), and wherein an M:P ratio above a predetermined threshold indicates a worse prognosis, and wherein the M:P ratio and the one or more CASs provide a measure of a level of risk and/or a prognosis associated with the cancer and indicate the severity of the cancer, the degree of intratumoral heterogeneity, or both.

2. The method of claim 1, wherein the method further comprises the step of determining a grade of the cancer, based on stratification provided by the M:P ratio.

3. The method of claim 1, wherein step (c) comprises flow cytometry to determine the percentages of mitotic cells and proliferating cells.

4. The method of claim 1, wherein the first binding agent targets a phosphorylated form of histone H3 and wherein the second binding agent targets Ki-67.

5. The method of claim 1, wherein the patient is treated with at least one antineoplastic agent based on the results from step (d).

6. The method of claim 5, wherein the at least one antineoplastic agent is selected from the group consisting of anti-mitotic agents, anti-interphase agents, anti-microtubule agents, anthracycline-based agents, and aromatase inhibitor agents.

7. The method of claim 1, wherein the patient is treated with at least one antineoplastic agent based on the results from steps (d) and (h).

8. The method of claim 1, wherein the patient is diagnosed with TNBC and wherein the M:P ratio is used to stratify TNBC into high cycling kinetics subclass or low cycling kinetics subclass.

9. The method of claim 1, further comprising the step of: treating the patient with chemotherapy.

10. The method of claim 1, further comprising the step of: treating the patient with chemotherapy and at least one additional antineoplastic agent.

* * * * *